United States Patent

Chin et al.

[11] Patent Number: 5,376,785
[45] Date of Patent: Dec. 27, 1994

[54] OPTICAL DISPLACEMENT SENSOR UTILIZING OPTICAL DIFFUSION

[76] Inventors: Philip K. Chin, 813 W. Wlm. David Pkwy., Metairie, La. 70005; P. Michael Lynch, 7332 Strathmore Dr., New Orleans, La. 70128

[21] Appl. No.: 955,932

[22] Filed: Oct. 2, 1992

[51] Int. Cl.$^5$ .............................. H01J 3/14
[52] U.S. Cl. .................. 250/214 PR; 250/227.21; 250/229
[58] Field of Search ............... 250/221, 227.21, 229, 250/231.13, 214 PR, 561; 341/31

[56] References Cited

U.S. PATENT DOCUMENTS

| | | | |
|---|---|---|---|
| 1,985,044 | 12/1934 | Lyle | 250/214 PR |
| 2,896,086 | 7/1959 | Wunderman | 250/214 PR |
| 3,859,617 | 1/1975 | Oka et al. | 250/214 PR |
| 4,114,035 | 9/1978 | Herzog | 250/214 PR |
| 4,271,354 | 6/1981 | Shellenberger | 250/214 PR |
| 4,320,293 | 3/1982 | Guretzky | 250/214 PR |
| 4,333,009 | 6/1982 | Stevens | 250/227.21 |
| 4,554,451 | 11/1985 | Kirstein | 250/214 PR |
| 4,607,160 | 8/1986 | Sakakino | 250/227.21 |
| 4,692,613 | 9/1987 | Masuda et al. | 250/214 PR |
| 4,739,163 | 4/1988 | Gambs et al. | 250/227.21 |
| 4,928,008 | 5/1990 | Huggins et al. | 250/214 PR |
| 4,994,669 | 2/1991 | Stern | 250/229 |
| 5,155,355 | 10/1992 | Kabaya | 250/214 PR |
| 5,194,919 | 3/1993 | Katayama | 250/229 |

FOREIGN PATENT DOCUMENTS 352069345  6/1977  Japan ........................... 250/214 PR Primary Examiner—Edward P. Westin
Assistant Examiner—Stephone B. Allen
Attorney, Agent, or Firm—Keaty & Keaty

[57] ABSTRACT

An optical displacement sensor is disclosed for use in robotic applications. The sensor can be used to examine the shape and surface texture of an object. In the embodiment which includes a compressible means of known spring constant, the sensor can be used to measure contract force. The position sensor uses an electro-optical displacement transducer to convert a displacement into an electrical output. The sensor utilizes a phototransistor to measure light emitted by an infrared light emitting diode. The amount of light received from by the phototransistor is varied by the displacement of the contact probe, or shadow rod.

59 Claims, 10 Drawing Sheets

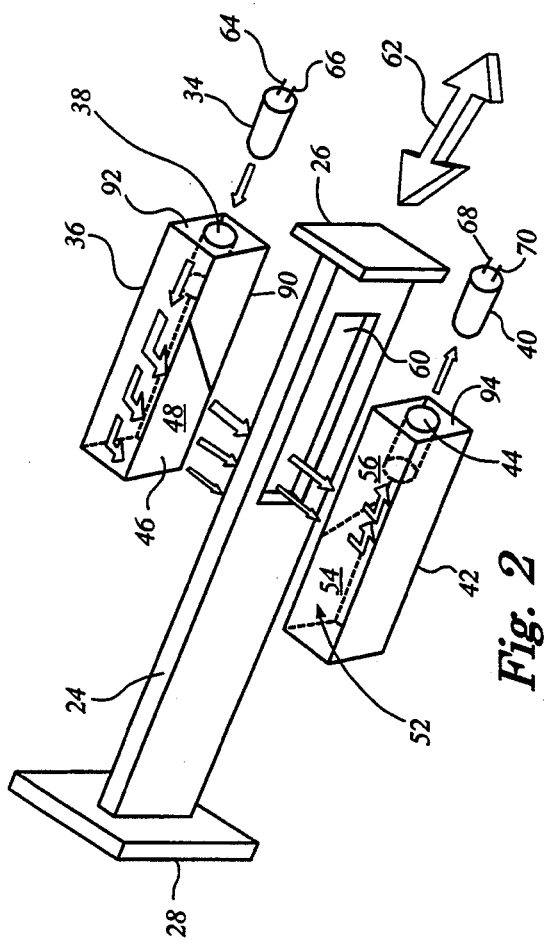
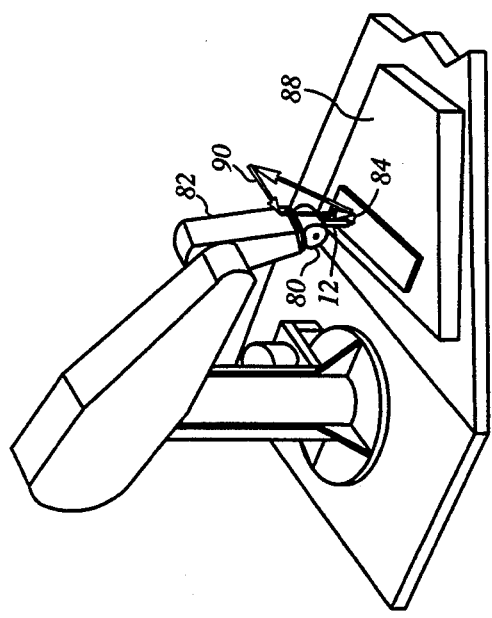
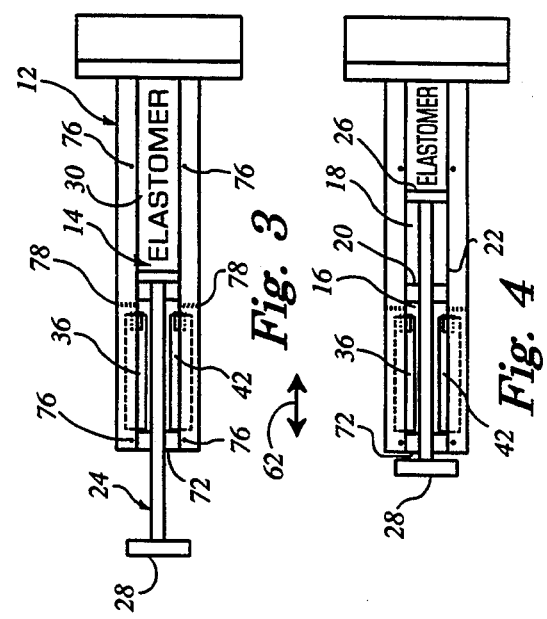
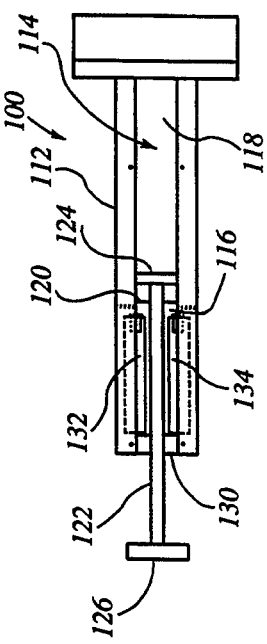

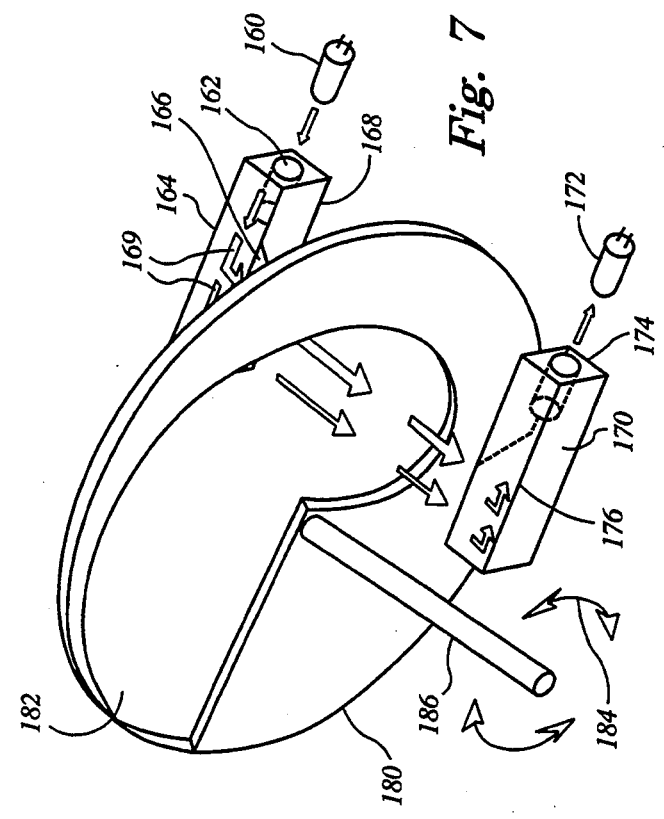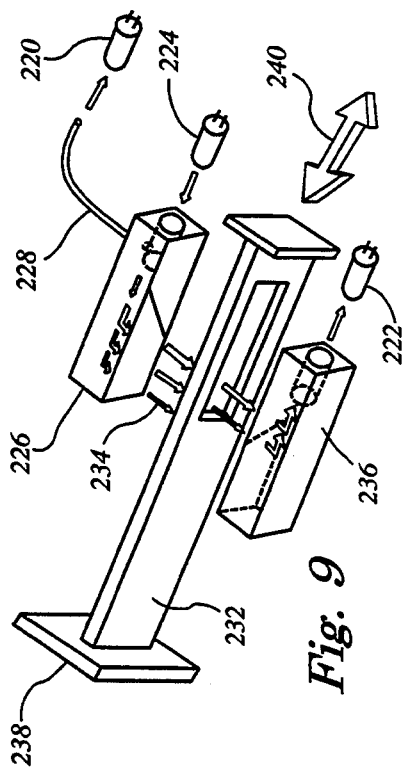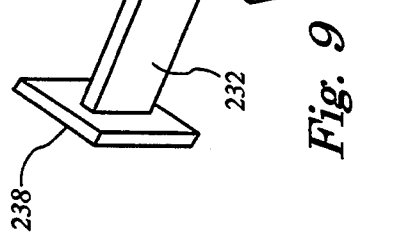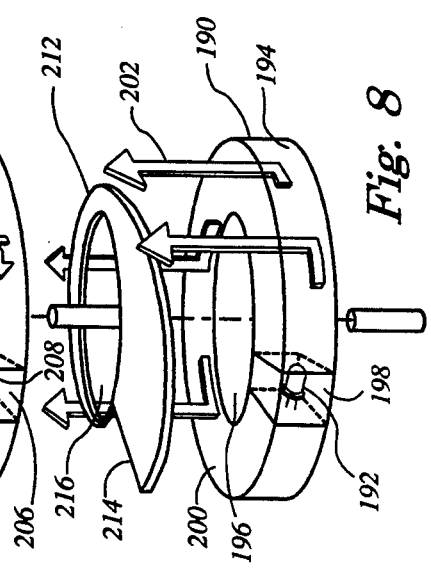

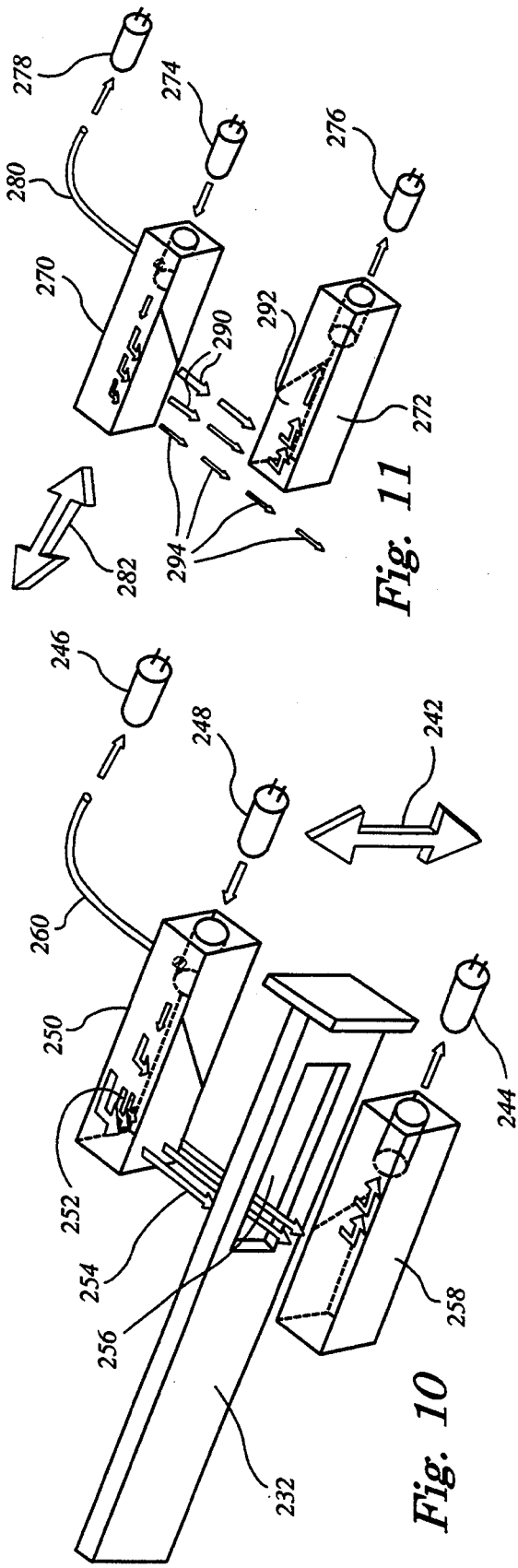
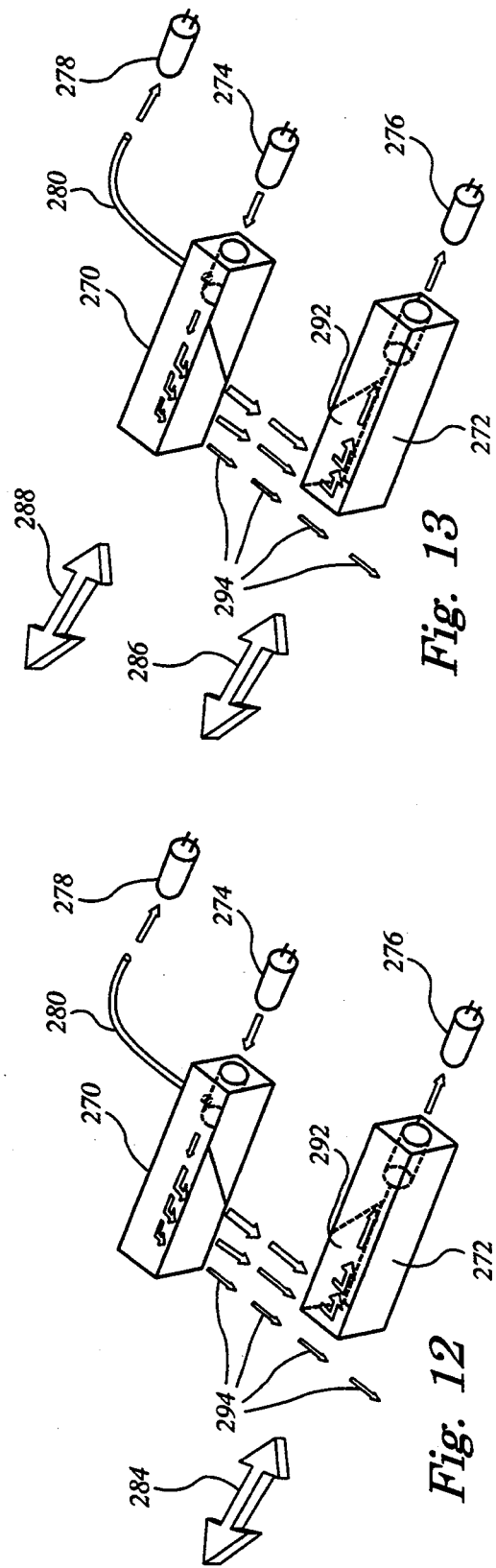

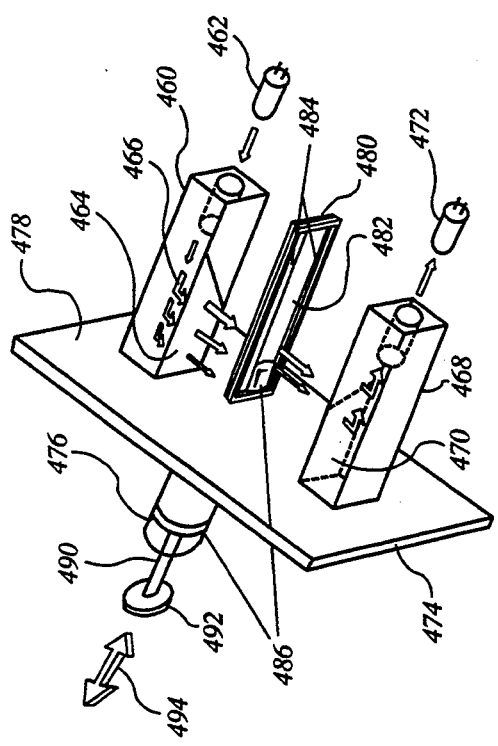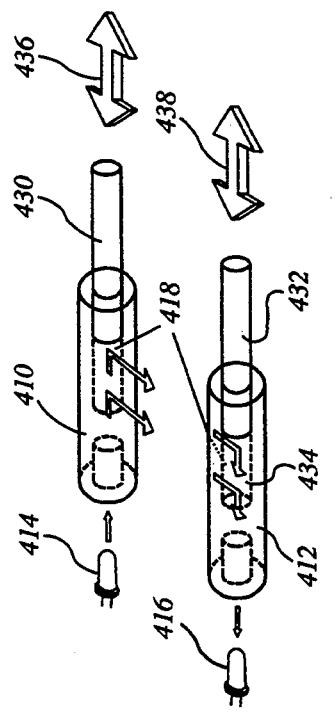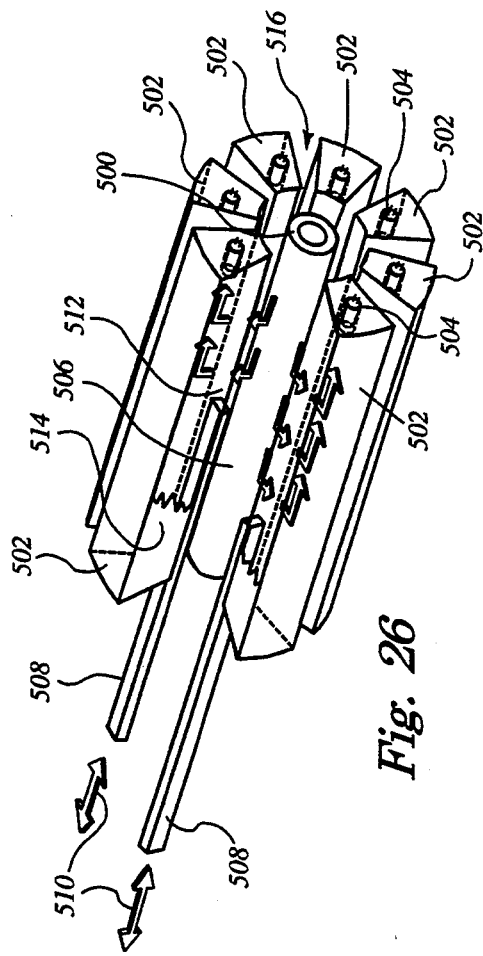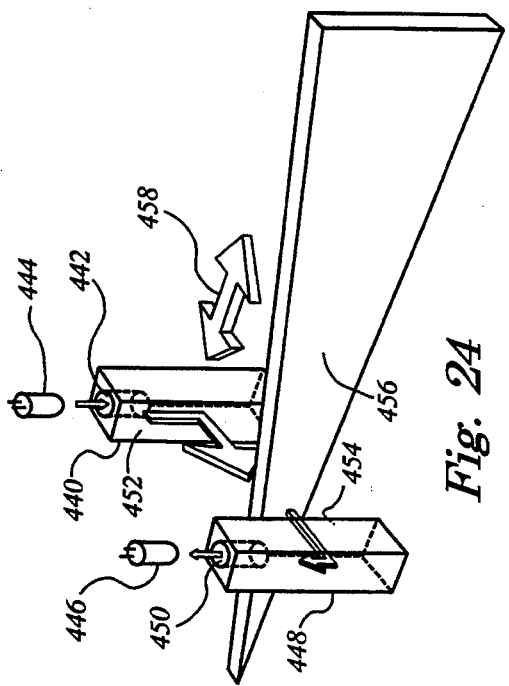

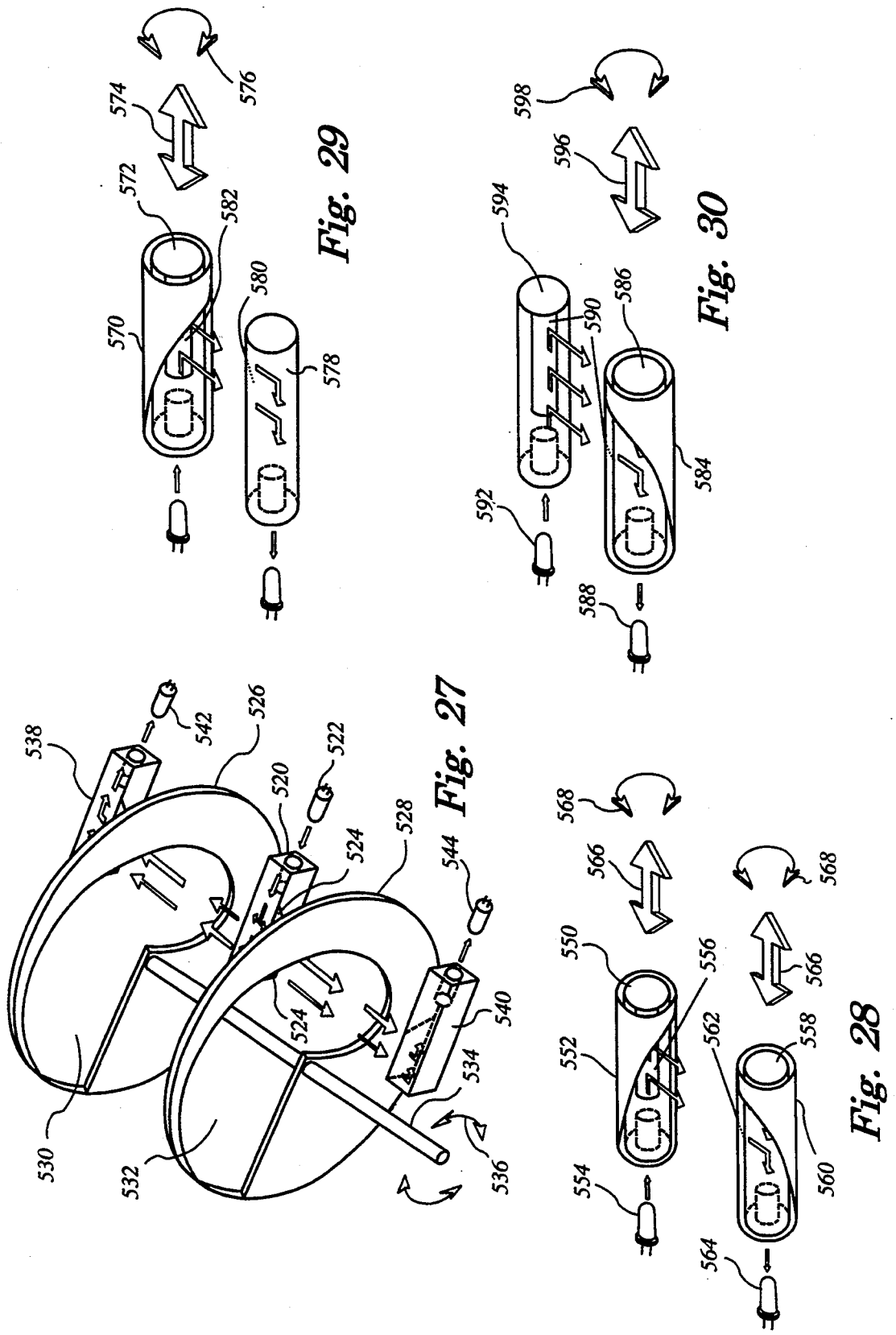

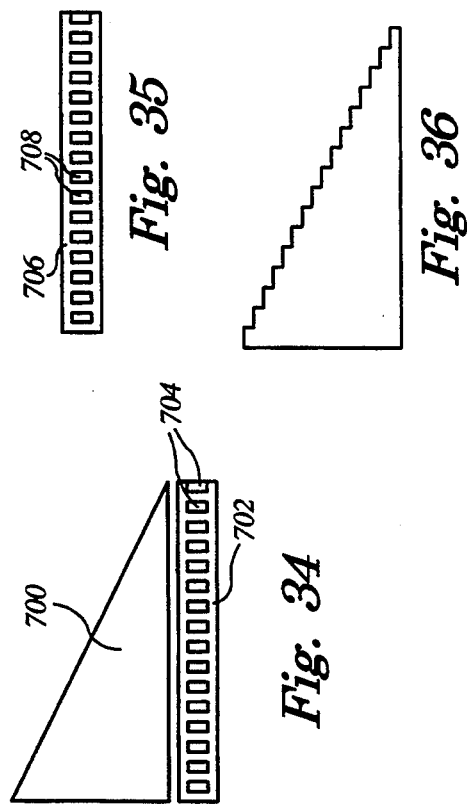
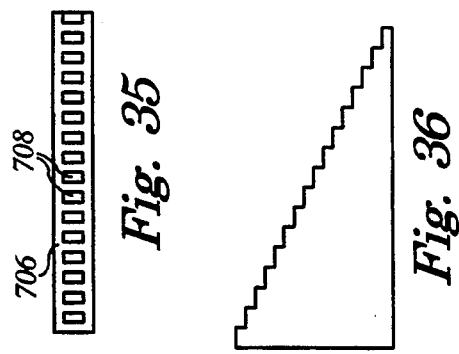
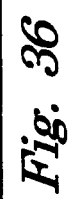
Fig. 33
Fig. 34
Fig. 35
Fig. 36
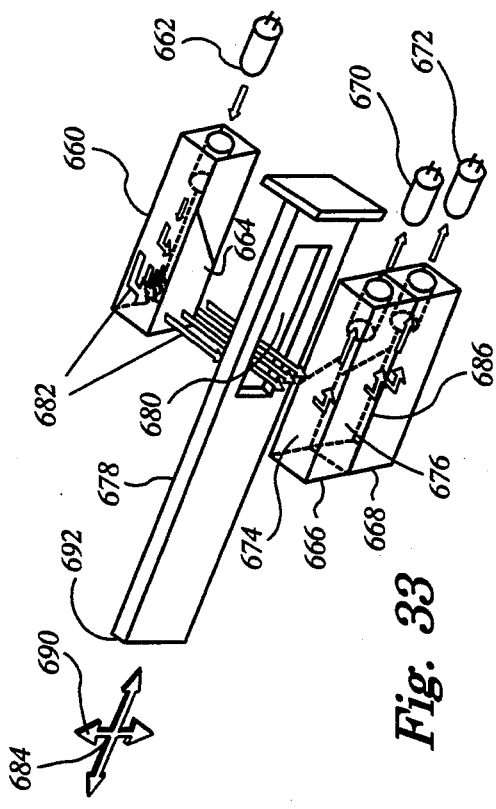
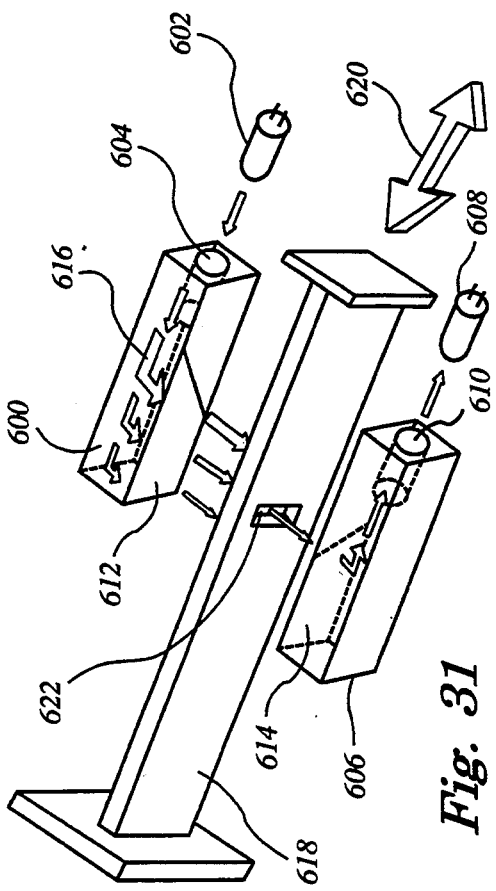
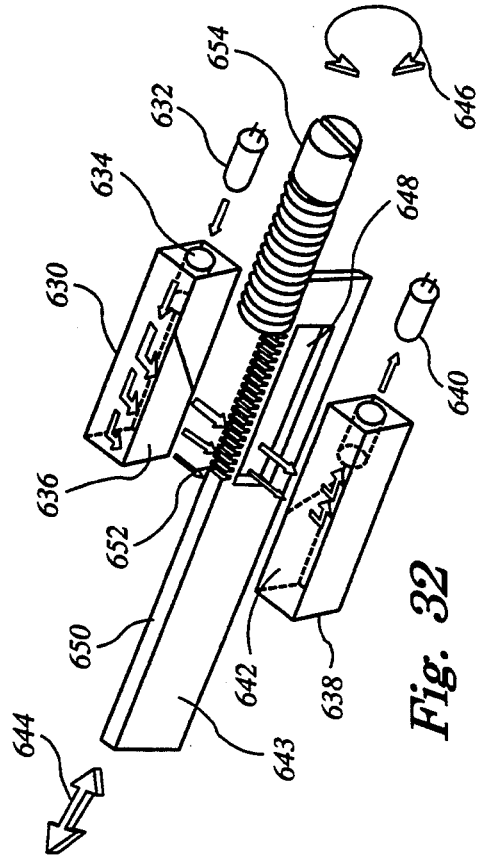
Fig. 31
Fig. 32

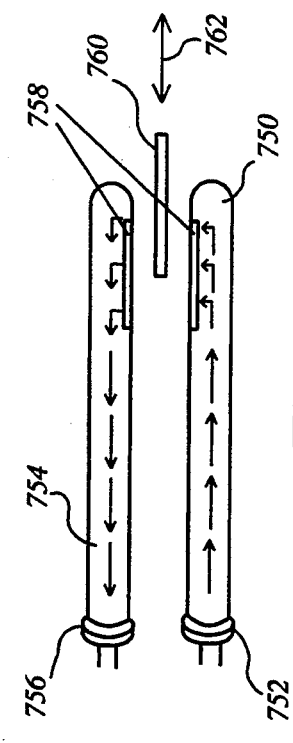
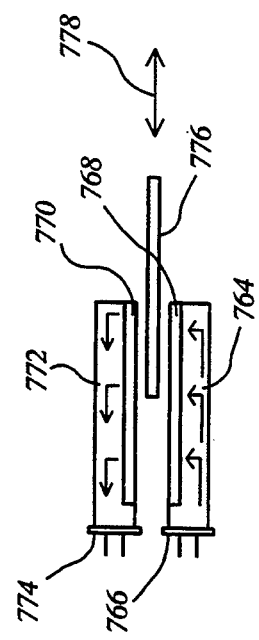
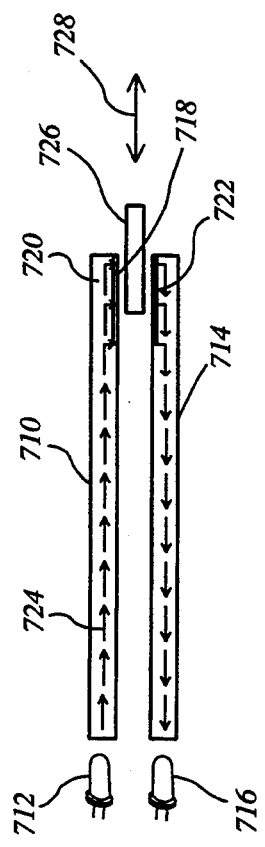
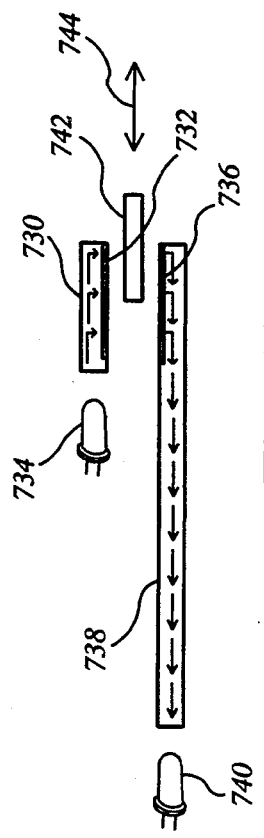
Fig. 37
Fig. 38
Fig. 39
Fig. 40

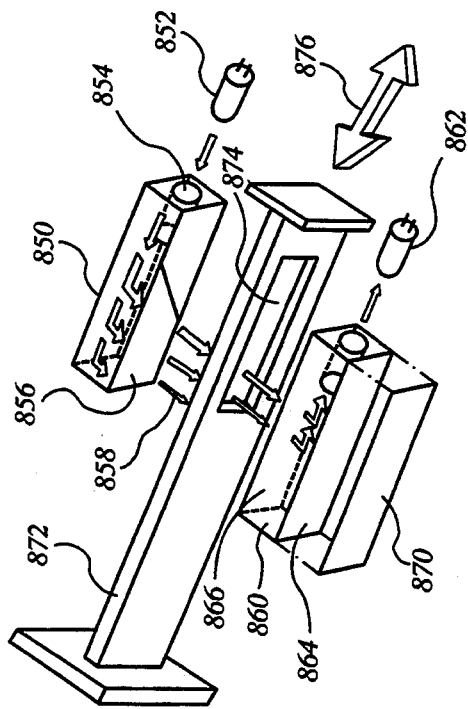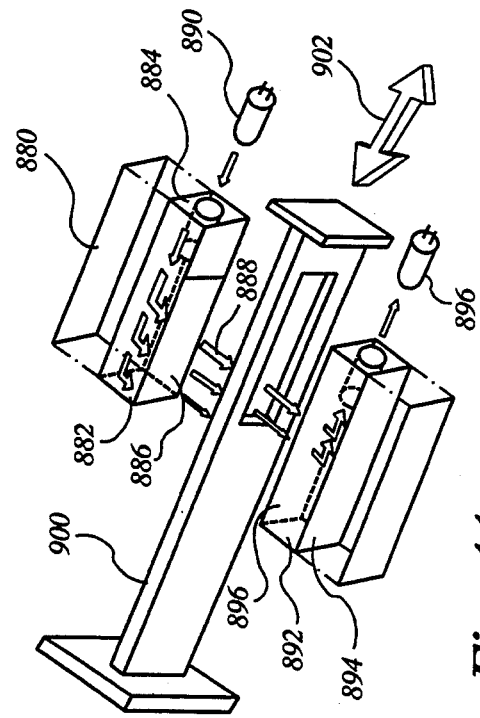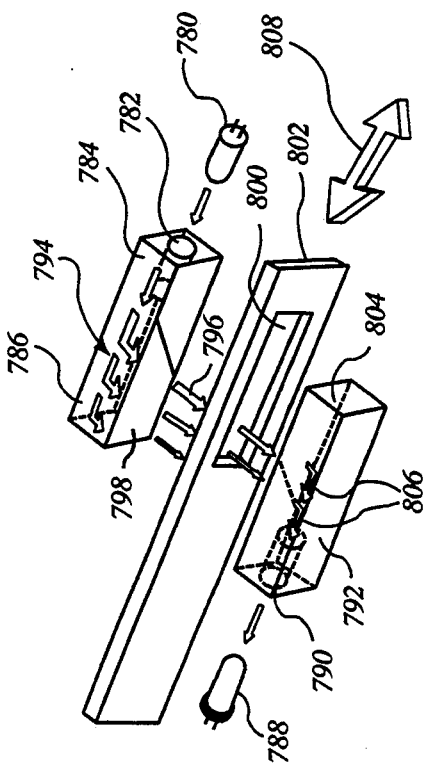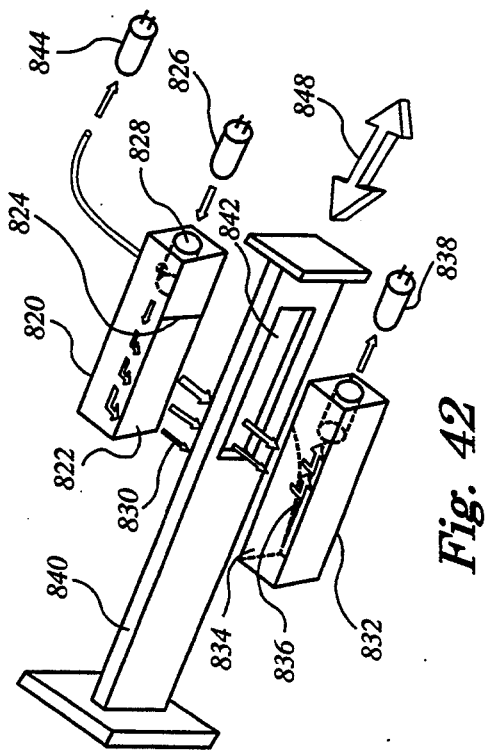

OPTICAL DISPLACEMENT SENSOR UTILIZING OPTICAL DIFFUSION

BACKGROUND OF THE INVENTION

This invention relates to a displacement sensor for use with robot end effectors in tactile operations, and more particularly to an optical displacement transducer.

In modern technologies, it is most important to use a robot which is capable of determining object shape through contact. For this purpose various types of displacement type transducers have been used, such as electrical transducers, which use various instruments to measure displacement, force transducers, which use a pliable solid to vary a certain electrical current, or optical displacement sensors, which measure the amount of light deflected from an object to determine its position, the present invention relates to the last-mentioned type of the transducer, the optical displacement sensor, which utilizes tactile sensing, that is information received through touch.

Since the optical sensors use light to transport information, they offer many advantages over electrical transducers, such as high sensitivity, versatility in design, and a high immunity to electromagnetic interference. Some of the optical displacement sensors use fiber optics to transmit and receive light reflected by an object. In fiber optic sensors a light emitting diode is used to emit light, which is reflected to a phototransistor.

Optical displacement transducers are sometimes used for the quality control of machined parts. These transducers, in some cases, use an occultation, or shadow method to produce an image into a camera for comparison with a "master" image. Micro-switches based on this principle are often used on assembly lines to detect the passage of an object and to record the number of items produced. The tactile sensors use a pair of emitter/detector hands arranged in arrays of sensors, which move in pre-determined directions, either in three axial directions, six axial displacements, etc. Some of the known optical tactile sensors use fiber optic cables which cross at right angles. The grid pattern is formed, and the grid junction surfaces of the optic cables are abraded to radiate light out of the sides of the fiber optic cables.

It is also important to note that robot sensors, in which the optical sensors are used, can be classified into internal and external state sensors. Internal state sensors detect the robot's joint positions. These type sensors include potentiometers and encoders in the motor of the robots.

External state sensors interact directly with the robot's surroundings. The external sensors can be contact and non-contact. The contact sensors are the sensors that measure physical contact with an object. These sensors detect force, torque, and/or pressure. Non-contact sensors sense objects with vision, light beams, and sound.

The present invention relates to a type of a transducer for use with a contact force sensor in detecting displacement of surface contours through the use of light.

SUMMARY OF THE INVENTION

It is, therefore, an object of the present invention to provide an optical type displacement transducer for robotic tactile applications.

It is another object of the present invention to provide a high accuracy, high sensitivity sensor using an IRLED/phototransistor.

It is a further object of the present invention to provide an optical displacement sensor which is inexpensive to manufacture and has a large dynamic range.

It is still a further object of the present invention to provide an optical displacement transducer which is durable and highly reliable.

The optical type displacement transducer of the present invention, in all of its embodiments, comprises an optical portion, which is formed by a light emitting means, a light receiving means, and some type of a light blocking means movable between the light emitting means and the light receiving means to intermittently block the light flow from a light source to the light sensor. The light blocking means can be formed as a non-permeable rectangular or spirally-shaped body adapted for linear and/or rotational movement in response to an externally applied force. The light blocking member has a window which allows the light flow to pass therethrough when the window is in alignment with the light flow. The window can be rectangular, square, or triangular in shape. Alternatively, a plurality of such windows can be positioned along the length thereof. The light blocking member can be a solid shadow rod in some of the embodiments, with a rectangular, triangular or square window in other embodiments. The light blocking means can be in the form of a discrete amount of light-impermeable liquid. In still other embodiments, a spiral rotational disk having a spiral window therein can be a light blocking means. The light emitting pipe can be in the form of a rectangular solid having an interior chamber therein, which is defined by an abraded face to facilitate diffusion of the light emitted by a light source mounted within the chamber. In alternative embodiments, the light emitting housing can be toroidially shaped with a central opening formed therein, a cylindrical body with a curved light permeable face formed in one end of the portion thereof or a prism-shaped housing.

The light receiving means can be a single solar cell or a plurality of light receiving bodies having a chamber therein, which houses a light sensor. The light receiving bodies can be one or more in number, positioned in circumferential relationship about the light emitting housing, in a juxtaposed relationship to each other and in parallel relationship to the light emitting housing, or in a linearly parallel relationship to the housing. The light blocking means can be also in the form of a compression spring, a triangularly-shaped body to gradually vary the amount of light transmitted along the horizontal and the vertical plane, or as a sleeve mounted in circumferential relationship about a light receiving means and/or light emitting means.

In a more specific preferred embodiment the device of the present invention provides for the use of a photodisplacement transducer which comprises an elongated hollow housing with a central chamber formed therein. A partition having a non-translucent surface divides the central opening therein to allow a slidable plunger to move in a slidable engagement therethrough. The plunger extends in substantially coaxial relationship with the central axis of the housing and moves in an axial direction between a fully extended position and a plurality of compressed, or partially compressed positions inwardly, toward the opposite end of the housing.

One end of the housing is blocked by an outer end plate which allows the plunger to pass therethrough to the exterior of the housing. A light emitting means and a light receiving means are mounted on opposite sides of the plunger within the first portion of the central chamber.

The light emitting means comprises an infrared light emitting diode which is positioned within an emitter light pipe, one surface of which faces the plunger. At least a portion of the facing surface is made translucent to allow the light to travel from the light emitting diode through the translucent face outside of the emitter light pipe. The light receiving means comprises a phototransistor mounted within a receiving light pipe, which has a surface facing the opposite side of the plunger. That surface, similar to the surface of the emitter light pipe, has a translucent portion which allows light to travel into the receiving light pipe and to the phototransistor.

The plunger serves as the light blocking means, or shadow rod, and may have a window opening adjacent to one of its ends. When the shadow rod moves within the housing, it partially, or completely blocks the translucent faces of the light emitting pipe and the light receiving pipe. Based on the amount of light passing through the window to the phototransistor, calculations can be made on the displacement value of the contact surface of the plunger.

In an alternative embodiment of the invention, a compressible means with a known spring constant is positioned within the second portion of the central chamber. The compressible means can be an elastomeric block, a coil spring, a leaf spring, a pneumatically movable piston, and the like. The compressible means continuously urges the plunger outwardly of the housing, and the plunger compresses the compressible means when contacting the surface being measured.

BRIEF DESCRIPTION OF THE DRAWINGS

Reference will now be made to the drawings, wherein like parts are designated by like numerals, and wherein FIG. 1 is a perspective view of the optical displacement sensor positioned on the end of a robot arm.

FIG. 2 is an exploded view of the optical portion of the device in accordance with the present invention.

FIG. 3 is a schematic view of one embodiment of the device in accordance with the present invention with a plunger in a fully extended position.

FIG. 4 is a schematic view of the device of FIG. 3 with the plunger in a compressed position.

FIG. 5 is a schematic view of another embodiment of the device in accordance with the present invention with a plunger in a fully extended position.

FIG. 6 is a schematic view illustrating in schematic form a shadow sensor design in accordance with the present invention utilizing a solar cell.

FIG. 7 is still a further embodiment of the optical displacement sensor in accordance with the present invention illustrating a rotational shadow sensor.

FIG. 8 is a schematic view illustrating the light emitting/transmitting portion of the rotation ring shadow sensor of still another embodiment of the apparatus in accordance with the present invention.

FIG. 9 is a schematic illustration of the optical portion of the displacement sensor of still another embodiment illustrating two light sensors.

FIG. 10 is a schematic illustration of the optical portion of the embodiment shown in FIG. 9, with a shadow rod moving in a different direction.

FIG. 11 is a schematic view of an optical portion of the displacement sensor, wherein an emitter light pipe is movable.

FIG. 12 is an embodiment similar to FIG. 11, but showing movement of a receiving light pipe.

FIG. 13 is similar to the embodiment of FIGS. 11 and 12, but illustrating movement of both emitter light pipe and the receiving light pipe.

FIGS. 21, 22 and 23 illustrate the use of circular tube sensors with the shadow rod moving in either the emitting light pipe or the receiving light pipe.

FIG. 24 illustrates an embodiment of the optical portion, specifically suitable for extended lengths of displacement.

FIG. 25 illustrates a further embodiment of the present invention, wherein a colored liquid is used as a shadow sensor.

FIG. 26 illustrates another embodiment of the design in accordance with the present invention utilizing multiple light sensors with a single light source.

FIG. 27 illustrates a further embodiment of the design of the present invention, which can produce multiple outputs with a single input.

FIGS. 28, 29 and 30 illustrate still further embodiments of the present invention utilizing circular tube sensors.

FIG. 31 illustrates an alternative embodiment utilizing a small size window in the shadow rod.

FIG. 32 illustrates still a further embodiment of the optical portion of the device in accordance with the present invention utilizing a "worm" shadow sensor.

FIG. 33 illustrates a further embodiment of the optical portion of the design in accordance with the present invention utilizing dual light sensors.

FIGS. 34, 35, and 36 illustrate different embodiments of the shadow rod and/or window in the shadow rod.

FIGS. 37 and 38 illustrate two embodiments utilizing extended light pipes.

FIG. 39 is a perspective schematic view of the unitary construction of the light pipes with the light source and the light sensor.

FIG. 40 schematically illustrates the unitary construction of the light pipes with the light source and the light sensor with extended translucent faces.

FIG. 41 is a schematic view illustrating a reverse direction shadow sensor for creation of a differently-shaped light flow path.

FIG. 42 is a schematic view illustrating a method of forming an altered signal curve output by changing translucent faces of the light receiving pipe and the light emitting pipe.

FIG. 43 is a schematic view illustrating a method of redirecting the light flow towards the light sensor in a later stage of the light flow.

FIG. 44 is a schematic view illustrating a method of affecting the light flow by redirecting the flow toward the light sensor in a later stage.

DETAILED DESCRIPTION OF THE PREFERRED EMBODIMENT

Figure 14:
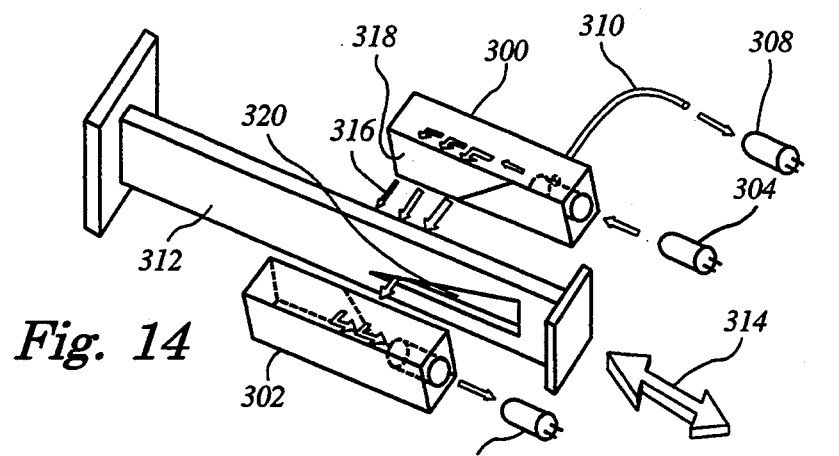
FIG. 14 is still another embodiment of the optical displacement sensor in accordance with the present invention, wherein a differently shaped window in the shadow rod is utilized.

Turning now to the drawings in more detail, the device of the first embodiment of the present invention is designated by numeral 10 in the drawings. The sensor has a housing cover 12 which is configured and sized to enclose the working part of the sensor. The housing 12 is an elongated body which is made from a lightweight, sturdy material, such as for example aluminum, and has an internal chamber 14 therein.

The chamber 14 is divided into a first portion 16 and a second portion 18 by a fixedly attached inner wall glide block 20. Extending through a central opening 22 of the glide block 20 is a plunger 24 which has an internal end provided with an inner end plate 26 and an external end carrying an outer end plate 28.

The end plate 26 is sized an shaped to frictionally engage the interior walls of the housing 12 and contact a compressible means 30 which is positioned in the chamber portion 18. The compressible means can be made of rubber, or other suitable material in the form of a coil spring, leaf spring, pneumatic piston, and the like which is compressible, resilient and durable to withstand multiple compressions.

The opposite surface of the plate 26 contacts the glide block 20, when the plunger 24 is in its fully extended position.

Mounted within the chamber portion 16 is an infrared light emitting diode (IRLED) 34 which is received within an emitter (IRLED) light pipe 36, and more particularly in a chamber 38 made specifically to house the diode 34.

The IRLED light pipe 36 can be in the shape of a rectangular solid, as illustrated in FIG. 2, or other suitable shape. The emitter light pipe 36 is made of a light transparent material, for example clear acrylic, to allow transmission of light from the light emitting diode 34 to a light receiving infrared phototransistor 40 which is mounted within its own receiving light pipe 42 on the opposite side of the plunger 24, in the chamber 44 formed in the light pipe 42. The receiving light pipe 42, similar to the light pipe 36, is formed from a transparent material, such as clear acrylic, and allows transmission of light emitted by the diode 34 to the phototransistor 40.

The light pipes 36 and 42 are designed to redirect and spread out the light and also to concentrate and redirect the light. This goal was achieved through preparing one of the surfaces 46 of the light pipe 36, so as to produce a translucent face 48. The translucent face 48 can be achieved through roughening of the surface 46, so that the surface is non-smooth.

The translucent face 48 causes the light emitted by the diode 34 to flow out of the face 48 of the light pipe 36 more diffusely. The other portion 50 of the surface 46 is formed non-translucent in order to channel the light in the desired direction.

One of the surfaces 52 of the light pipe 42 is likewise divided into a translucent portion 54 and a non-translucent portion 56.

A window opening 60 is made in the plunger 24 to allow the light to travel from the diode 34 through the translucent face 48 to the translucent face 54 and then to the receiving phototransistor 40.

It will be appreciated, that when the plunger 24 moves in an axial mariner, in the direction shown by an arrow 62, the light will either be partially or totally blocked by the plunger 24, and transmitted to the face 54 of the light pipe 42 in the first instance. The amount of light transmitted to the face 54 varies with the position of the plunger 24, or "shadow rod". Therefore, depending upon its positions, the "shadow rod" 24 obstructs, or partially obstructs the light transmitted from the diode 34 to the phototransistor 40.

The IRLED diode 34 has a cathode 64 and an anode 66. The phototransistor 40 has an infrared phototransistor collector connection 68 and an infrared phototransistor emitter connection 70.

Since the position of the shadow rod 24 determines the amount of light received by the phototransistor 40, the amount of photocurrent (or base current X) is also controlled by the position of the plunger 24. This photocurrent then controls the connector 68 current of the input transistor (or the base current of the output transistor). The base current of the output transistor, in turn, controls the collector current of the output transistor. In order to measure an output voltage, the collector current is passed through a load resistor. As a result, the position of the shadow rod 24 determines the output voltage of the electrical circuit.

One of the exemplary methods of forming such a translucent surface can be treatment of the faces 48 and 54 by chemicals to form a light diffusive surface. Another method which can be successfully utilized is addition of chemicals to a formation mixture during fabrication of the light pipes so as to produce an internally light diffusant light pipes.

In the position of the plunger illustrated in FIG. 3 (fully extended position), the deflection is zero. The sensor is transmitting the maximum amount of light and producing the maximum output voltage. When the plunger is in the position illustrated in FIG. 4 (fully compressed position), the sensor is transmitting the minimum amount of light and producing the minimum output voltage.

It is envisioned that the deflections for full extension and full compression are between 0 inches and 0.8 inches, respectively. In some embodiments, this deflection will be the maximum deflection, beyond which the device 10 may be damaged.

The device 10 further comprises an outer end plate, or outer glide block 72, which is provided with a central hole to receive the plunger 24 therethrough. The glide blocks 72 and 20 can be covered with Teflon coating to allow plunger 24 to move freely, while shielding light from extraneous sources.

A cover plate (not shown) is attached to the housing body 12 by screws engagable in holes 76 made in the body 12.

The wire connections from the phototransistor 40 and from the diode 34 are allowed to exit the housing body 12 through corresponding openings 78 made in the body thereof.

When in use, the device 10 is connected with a voltage regulator, several resistors, potentiometer, output transistor, wire connectors and "bread" board (not shown). The voltage regulator is used to smooth the signal from the power source. The resistors and the potentiometer are used to adjust the voltage into the diode and the phototransistor, while the output transistor is designed to simplify circuit connections between the parts. The "bread" board is used to complete the circuit.

In operation, the position or displacement sensor 10 can be attached to a wrist 80 of a robot arm 82. The end 28 of the plunger 24 can be equipped with a sharp ended pointer 84 to provide a direct contact surface with the measured object, which is positioned on the plate 86. In this embodiment the device 10 can be used to measure contact force of the robot arm or an object.

If desired, the plate 86 can be placed on a high friction block 88 to prevent displacement of the plate 86, which could effect the results of the measurements.

The movements of the robot arm illustrated by arrows 90, with movements being multiple in number and gradual, so as to cover the entire surface of the measured object.

The overall speed of the sensor is generally determined by the speed of the electrical circuit used in the construction of the device 10, the mechanical dynamics of the sensor in contact with its surrounding, and the amount of friction between the plunger 24 and its contacting surroundings.

In one of the tested embodiments photodarlington circuits were used. If they prove to be too slow, it is envisioned that the circuit can be replaced with a photodiode circuit, or a Burras diode circuit or an edge-emitting LED circuit to improve the speed.

The design of the plunger 24 can be also amended to reduce the probe mass and coefficient of friction.

During tests, the maximum error between compression and extension readings of the device 10 corresponding to the same displacements was approximately 0.01 volts or 0.2315%.

It is suggested, that the glide blocks 20 and 72 be non-translucent, either colored or covered with black color, so as to overcome the semi-opacity of Teflon. For the same purpose, that is to prevent diffusion of light, the faces 92 and 94 of the light pipes 36 and 42, respectively, should be made non-translucent by covering them with a metallic tape similar to the surfaces 50 and 56.

It is also noted that errors can arise from electrical and magnetic interference and it is preferred that interference from these type of noises be reduced to a minimum. It is also preferred that the surface portions 48 and 54 be made translucent to bring the amount of light passing through those surfaces to a maximum. The remaining surfaces are preferably smooth and clear so as to reduce the amount of light lost through these other surfaces to a minimum.

These other surfaces can be made non-translucent, so as to further channel the light in the desired direction. One method of producing a non-translucent surface is covering the surface with mirror finish metallic stickers. Another exemplary method is similar to the one used in fiber optic telecommunications a special cladding is used the reduce the amount of light lost through the fiber optic cable.

FIG. 5 illustrates another embodiment of the optical displacement sensor, designated by numeral 100 in the drawings. The device 100, similar to the device 10, has a housing 112 made with an internal chamber 114 therein. The chamber 114 is divided into the first portion 116 and the second portion 118 by a partition 120, which has non-translucent surfaces and is fixedly attached to internal walls of the housing 112. The partition 120 serves as a glide block for an elongated plunger 122 which passes through the central opening formed in the partition 120.

The plunger 122 has an inner end plate 124 attached to its inner end and an outer end plate 126 attached to its outer end. One of the surfaces of the end plate 124 contacts the partition 120 when the plunger is in its most extended position. The partition 120 limits the movement of plunger 122 outwardly.

One of the ends of the housing 112 is closed by an outer end plate 130 through an opening, in which the plunger 124 extends from the housing 112.

The plunger 124 moves in co-axial sliding engagement within the housing, and its movement is not restricted by any compression means, which is absent in this embodiment.

The device 100 also has an emitter light pipe 132 and the receiving light pipe 134, provided with an IRLED diode and an infrared phototransistor, respectively. Operation and structure of the optical portion of the device 100 is similar to that of the device 10.

The sensors 10, 100 of the present invention are light-weight and can be successfully used as tactile sensors. The window openings in the plungers 24, 124 can be shaped to produce a linear output which will simplify the data processing. A high level of accuracy can be achieved, since the sensors use light as the transduction medium, and any outside electromagnetic interference will have no effect on the medium itself.

The minimum of the elements and parts of the sensors 10, 100 allows a relatively inexpensive manufacture of the product. The level of friction of the sensors 10, 100 is considerably lower than that of variable resistance transducers. The life and durability of the devices is longer than that of resistance transducers, since there is little wear. Additionally, the occultation technique has a much higher resolution than with the wire resistance transducers. The sensors 10, 100 are easier to assemble than the linear variable differential transformer, while the occultation technique can produce a totally linear output, in comparison with a partial linear output produced by inductive method.

The operation of the devices 10, 100 is not limited by the use of special materials, while other transducers often require a certain material to function effectively, such as for example piezoelectric, magnetoresistive, and dielectric transducers.

Turning now to FIG. 6, a still further embodiment of the design of the present invention is schematically illustrated. As can be seen in the drawing, the sensor design incorporates a solar cell 140 in combination with the shadow rod 142 and a light source 144 positioned within an opening 146 of the light pipe 148. The solar cell 140 is equipped with connecting wires 150 for transmitting the output of the light receiving solar cell 140 to a distant independent computer.

The shadow rod 142 is illustrated as having a general rectangular shape. The shadow rod 142 can be formed with or without a light transmitting window depending on the specific design. The emitter light pipe 148 has a translucent face 154 which is formed by, for example, abrading that surface which faces the shadow rod 142. The remaining sides of the light pipe 148 are covered with non-transparent film, for example, metallic stickers, so as to channel the light from the light source 144 in the direction of arrow 156 towards the light receiving cell 140.

During operation, the shadow rod 142 moves in the direction of arrow 158 intermittently blocking and uncovering the light beam emitted by a light source 144 and exiting through the face 154.

If desired, the shadow rod 142 can be combined with a plunger, similar to the plunger 24, and the design of the displacement sensor utilizing the elements of FIG. 6 can incorporate a spring or elastomeric means for providing compliance during movement of the shadow rod 142. The spring and the elastomeric means can be similar to the embodiments illustrated in FIGS. 3-5.

Turning now to the embodiment of FIG. 7, a rotational shadow sensor of another embodiment of the device in accordance with the present invention is illustrated. As can be seen in the drawing, the optical displacement sensor is provided with a light emitting means 160 mounted within an opening 162 of an emitter light pipe 164. One surface of the light pipe 164 is divided into a first portion 166 and a second portion 168. The portion 166 is made translucent to allow movement of light in the direction of arrows 169 therethrough. The second part 168 of that surface is formed non-transparent and is for convenience covered with a reflective adhesive film, so as to channel the light in the desired direction.

The light travels to a receiver light pipe 170 and is detected by a light receiving means 172 mounted within an opening 174 formed in the receiver light pipe 170. The light which travels in the direction of arrows 169 is received through that portion 176 of the surface of the light receiving pipe 170 which faces the light pipe 164. The second portion 178 of the light pipe 170, as well as other surfaces are made non-transparent.

The light blocking means in the embodiment of FIG. 7 is made in the form of a spiral shadow disk 180 which produces a linear output curve from an angular displacement. The disk 180 is provided with a spiral-shaped window 182 which intermittently blocks or uncovers the light path traveling from the light emitting means 160 to the light receiving means 172. The rotation of the spiral shadow disk in the direction of arrows 184 allows the disk 180 to intermittently block the traveling light. A securing means, such as a rod 186, is provided in a fixed attachment to the spiral shadow disk 180 to allow mounting of the disk within an optical displacement sensor.

The surfaces 166 and 176 can be formed abraded or non-abraded, as desired, as long as the surface is translucent. It is envisioned that the embodiment of FIG. 7 can be particularly useful in measuring angular or rotational displacement. If desired, a spring means, in the form of a coil or an elastomer can be employed to provide a torsional compliance.

In the embodiment of FIG. 8, another version of a rotational shadow sensor is illustrated. As can be seen in the drawing, the optical portion of the device comprises a ring-shaped emitter light pipe 190 which houses a light source 192 therein. The emitter light pipe 190 has an annular surface 194, a circular opening 196 and a pair of opposing flat surfaces 198 and 200. The surface 200 is made translucent to allow transmission of light in the direction of arrows 202 outwardly from the light pipe 190 towards a ring-shaped receiving light pipe 204

The receiving light pipe 204 is provided with a light receiving face 206 and a light receiving sensor 208 is housed within the pipe 204. The light travels in the direction of arrows 210 within the receiving light pipe 204 until it reaches the light receiving means, for example, a light receiving diode 208. The beams of light are intermittently blocked by a rotating spiral shadow disk 212 which has a light blocking portion 214 and a window 216. The disk 212 rotates in the direction of arrows 216 in a clockwise or counter-clockwise direction.

An attachment means, for example an elongated rod 218, is secured to the disk portion 214 to allow transmittal of the necessary torque to the shadow disk 212. The spiral shadow disk 212 is designed to produce a linear output curve from an angular displacement and can be also used to measure rotational displacement. The surfaces 200 and 206 can be abraded to produce a more translucent surface. Similarly to the embodiment of FIG. 7, the optical portion of the embodiment in FIG. 8 can be incorporated into the optical displacement sensor which can be equipped with a spring means in the form of a coil, or an elastomer, so as to provide a torsional compliance.

Referring now to FIG. 9, an optical portion of the displacement sensor of still another embodiment is illustrated. This particular embodiment employs two light sensors 220 and 222 and one light source 224. The light source is mounted within an emitter light pipe 226, while the first light sensor 220 is connected to the light pipe by a fiber optic cable 228 for transmitting light from the light source 224 to the light receiving sensor 220. The use of the second light sensor is thought to be particularly useful in monitoring and calibrating the light source 224, so as to provide consistent readings over time and to compensate for temperature changes. The light source output is transmitted through a window 230, formed in the shadow rod 232, in the direction of arrows 234 towards a light sensor 222 mounted in the light sensor light pipe 236.

As will be appreciated, the embodiment shown in FIG. 9 is similar to the embodiment of FIG. 2 in all other respects, that is in provision of a plunger 238 and translucent surfaces which face each other on the emitter light pipe 226 and the receiving light pipe 236, respectively. The direction of the plunger movement is schematically shown by arrow 240 in FIG. 9. It is envisioned that an optical light sensor can be provided in order to monitor the light source output.

Referring now to FIG. 10, the optical portion of the displacement sensor similar to the embodiment of FIG. 9 is illustrated. This drawing illustrates movement of the shadow rod 232 in a direction shown by arrow 242 which is perpendicular to the direction shown by arrow 240. While this embodiment also employs a pair of light sensors 244 and 246 and one light emitting source 248, the light travels from the light pipe 250 in the direction of multiple vertical level arrows 252. As can be seen in FIG. 10, a portion of the light beam, which is schematically illustrated by arrow 254, will not pass through the open window 256 made in the shadow rod 232, but will be blocked by the solid wall of the shadow rod 232. The remainder light will travel to the receiving light pipe 258 and will be received by the light sensor 244. The second light sensor, sensor 246, may be connected to the light pipe 250 by a fiber optic cable 260, similarly to the fiber optic cable 228.

It is envisioned that when the shadow rod moves in the direction perpendicular to the plane of the light flow, the optical displacement sensor can be particularly useful in detection of torque couples and shear forces in tactile applications. An example of such application is detection of object slippage from a robotic hand.

Turning now the embodiments of FIGS. 11, 12 and 13, the optical portion of a displacement sensor of a further embodiment is illustrated. Similarly to the previous embodiments, the optical portion comprises an emitter light pipe 270, a receiving light pipe 272, a light source 274 positioned within the light pipe 270, and a receiving light sensor 276 positioned within the receiving light pipe 272.

Additionally, a second light sensor 278 is optically connected, through the use of a fiber optic cable 280, if desired, to the emitting light pipe 270. The fiber optic is used to calibrate and/or monitor light source, but may be omitted, if desired. In the embodiment shown in FIG. 11, the light pipe 270 is made movable in the direction of an arrow 282, while the emitter light pipe 272 remains stable. No plunger is used in the embodiments of FIGS. 11, 12 and 13, such that the displacement output depends on the amount of movement of either the light pipe 270 (embodiment of FIG. 11), of the receiving light pipe 272 (in the embodiment of FIG. 12) or mutual relative displacement of the light pipes 270 and 272, as shown in the embodiment of FIG. 13. For the purposes of simplification, the movement of the receiving light pipe is illustrated as directional arrow 284, while the displacement of both the receiving light pipe and the emitting light pipe is schematically shown by arrows 286 and 288, respectively.

As can be seen in the drawings, a certain portion of the light beam which is emitted from the light pipe 270 is received by the receiving pipe 272. This portion is schematically illustrated in the drawings and is designated by numeral 290. At the same time, when either or both the emitter pipe and the receiving pipe are displaced in relation to each other, a certain portion of light will "miss" the receiving light pipe 272 and will pass outside of the receiving surface 292 of the receiving light pipe 272. That portion of the light energy is schematically illustrated by arrows 294 in the drawings.

With regards to the embodiment of FIG. 13, regardless of whether emitter and/or receiver light pipe are displaced, there will be a dual displacement input but one single sensor output. It should be noted, that the structure of the light pipes 270 and 272 is similar to the structure of the light pipes 250 and 258.

Turning now to the embodiment of FIG. 14, the optical portion of a displacement sensor of still another embodiment of the present invention is illustrated. As can be seen in the drawing, the optical portion is similar to the previous embodiments, in that it comprises a light emitting pipe 300, a light receiving pipe 302, with a light emitting pipe housing a light source 304 and the light receiving pipe housing a light receiving sensor 306. A secondary light sensor 308 can be optionally connected to the light emitting pipe 300 through a fiber optic cable 310. The plunger 312 in this embodiment moves longitudinally between the light pipes 300 and 302 in the direction of arrow 314, intermittently blocking and uncovering the light beams 316 emitted by the light emitting means 304 and passing through the face 318. As shown in the drawing, the window 320 formed in the plunger 312 is formed in a triangular shape to form an output curve which is not linear. By changing the window shape of the shadow rod, different signal output curves can be obtained in a certain number of desirable applications.

Figure 15:
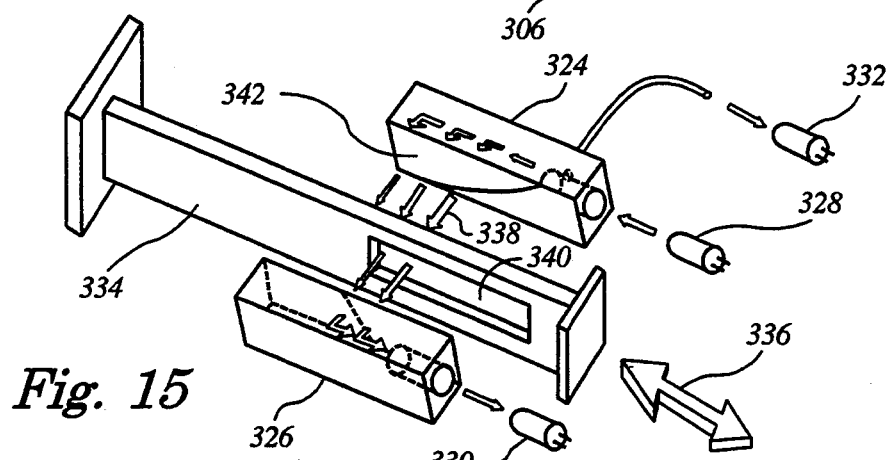
FIG. 15 illustrates still a further embodiment of the device in accordance with the present invention, wherein the shape of a translucent face was altered.
Figure 16:
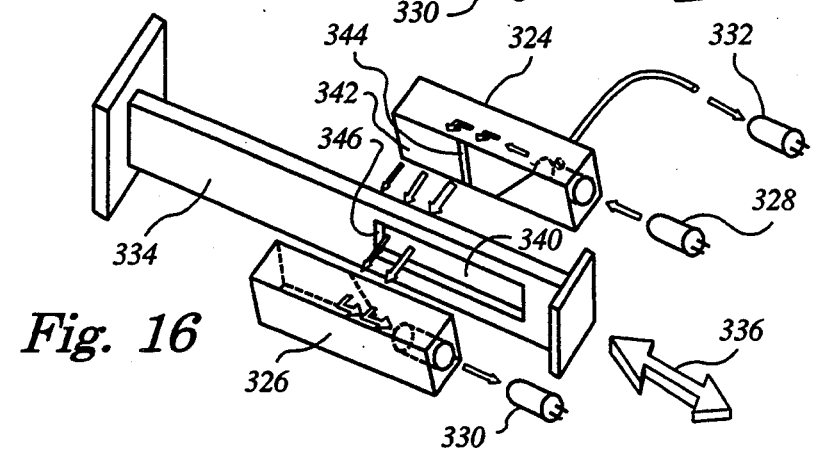
FIG. 16 is similar to FIG. 15, but schematically illustrates provision of a null space in a translucent face.
Figure 17:
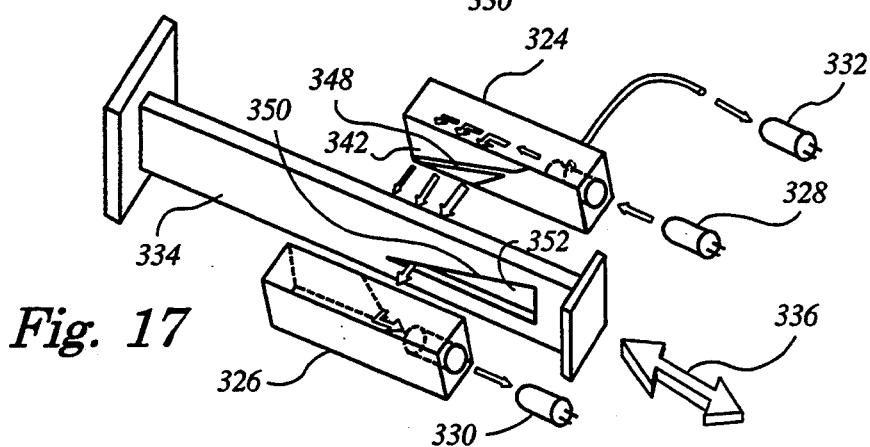
FIG. 17 is similar to the embodiment of FIG. 16, wherein the translucent face was altered through a provision of a null space made on a diagonal.

It is also possible to change the shape of the signal curve by altering the translucent face of the emitting and/or receiving light pipe. In the embodiments shown in FIGS. 15, 16 and 17 such changes were made. The embodiments of FIGS. 15, 16 and 17 are similar to each other and each are shown to comprise a light emitting pipe 324, a light receiving pipe 326, a light source 328 and a pair of light sensors 330 and 332. The movable plunger 334 moves in the direction of arrow 336, alternatively blocking and uncovering light beam schematically shown by arrows 338 which pass through the window 340 formed in one end of the plunger 334. The translucent face 342 of the light emitting pipe 324 was changed to resemble an exponential curve about the lower boundary thereof. As a result, a different shape of the signal curve is received by the output sensor.

In the embodiment of FIG. 16, the translucent face 342 of the emitting light pipe 324 was amended by forming a reflective separation line, or null space 344 dividing the entire translucent surface 342 into two portions. It should be noted that when the left edge 346 of the window 340 aligned itself with the line 344, there was no detected change in the light sensor's signal output. It is envisioned that such null space or non-translucent separation line can be useful in applications with, for example, a joystick, where no cursor movement is desired when the joy stick is in the center position. The same possible application can be obtained with the embodiment of FIG. 17, wherein a null space created by a diagonal line 348 made in the translucent face 342 of the light emitting pipe 324, generally matches the angle of direction of the top edge 350 of the triangular window 352 formed in the shadow rod 344. When the lines 348 and 350 are aligned, there are no changes in the light sensor's signal output.

Turning now to the embodiments of FIGS. 18 and 19, the use of a spring means as a shadow sensor will be discussed. As can be seen in the drawings, the provision of the emitting light pipe 360 with an associated light source 362, as well as a receiving light pipe 364 and associated light receiving means 366 is common to the previously described embodiments. Similarly, the light pipes 360 and 364 are both provided with translucent faces 368 and 370, respectively, to allow emission and receipt of the light emitted by the light source 362 and detected by the light sensor 366.

Figure 18:
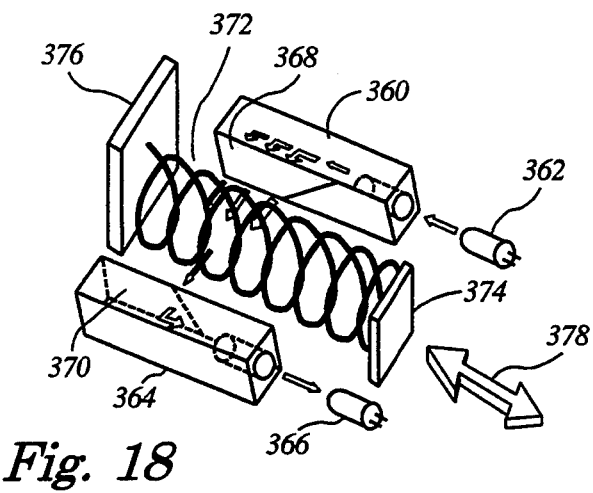
FIG. 18 illustrates still a further embodiment of the optical portion of the design of the present invention, utilizing a spring means to block a light flow, with the spring in a compressed position.
Figure 19:
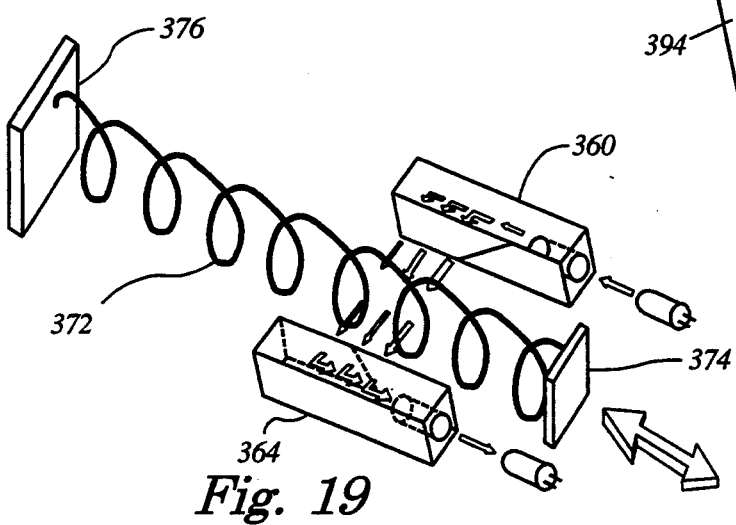
FIG. 19 is an illustration of the embodiment of FIG. 18, with a spring means in an extended position.

However, the embodiment of FIGS. 18 and 19 differs in the part of the shadow rod, wherein a spring means, in the particular embodiment illustrated shown as a coil spring 372, is disclosed. The spring 372 is mounted between two plates, a stable securing plate 274 and a moving contact plate 376. The plate 376 moves laterally in the direction of movement illustrated by arrow 378 intermittently compressing and expanding the coil spring 372, so as to control the amount of light flow from the light source 362 to the light sensor 366.

As will be appreciated, when the spring 372 is in a compressed position, the spring will limit the amount of light flow from the light source to the light sensor. However, when the spring 372 is extended from its contracted position of FIG. 18 and appears in the condition that is illustrated in FIG. 19, the amount of light allowed to reach the light receiving pipe 364 increases. In the embodiment shown in FIGS. 18 and 19, the spring means, in the shape of the coil spring 372 performs the compliance functions, as well as the occultation function.

Referring now to the embodiment of FIG. 20, the use of prism-shaped light pipes will be discussed. As can be seen in the drawing, the light emitting pipe 380 has an opening 382 therein which receives a light source 384. The walls defining the opening 382 can be roughened, for example abraded in order to further diffuse the light being transmitted from the light source 384. A light receiving pipe 386, similarly, has an opening 388 formed in its base surface to receive a light sensor 390 therein. The walls defining the opening 388 can be abraded to form a translucent surface for better light diffusion qualities. The diagonal faces 392 and 394 of the light emitting pipe 380 and of the light receiving pipe 386, respectively, can either have an adhesive reflective film secured thereon and/or can have their surfaces abraded to produce a light diffusive face. As a result, the light flow is forced to exit the light pipe 380 in the direction of arrow 396 (a bent arrow) and enter the light pipe 386 in the direction of arrow 398 to reach the light sensor 390. The use of inverted prisms produces a light flow of a special character.

Figure 20:
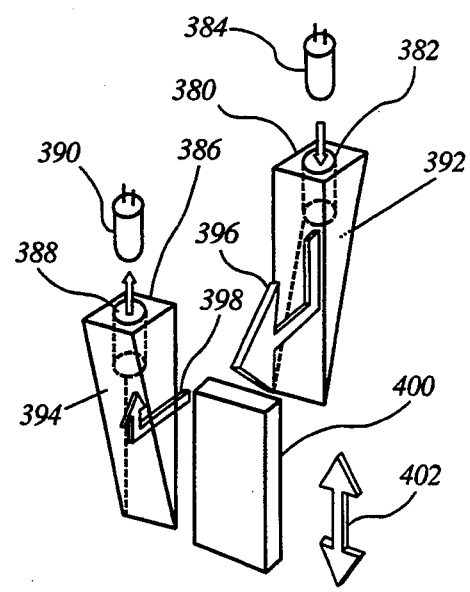
FIG. 20 illustrates a further embodiment of the design in accordance with the present invention, utilizing prism-shaped light pipes.

A shadow rod 400 which moves between the light pipes 380 and 386 to intermittently block the light flow emitted by the light source 384 and received by the light sensor 390 can be in the form of a rectangular solid shown in FIG. 20 or in other forms, as desired. For example, the shadow rod can be made with a window similar to the embodiment of FIG. 2 and others, can be also made with inner and outer plungers, if so desired. The direction of the shadow rod movement is indicated by arrow 402 in FIG. 20.

Turning now to the embodiments of FIGS. 21 and 22, the use of tubular-shaped light pipes will be discussed. The embodiments illustrated in both figures are similar, in as much as they utilize a light emitting pipe 410 and light receiving pipe 412, each formed with corresponding openings to receive a light emitting diode, or other light source 414, and a light sensor 416, respectively. The surfaces 418 on both light pipes 410 and 412 are made translucent for light diffusion purposes. The remainder surface of the light pipes 410 and 412 is made non-translucent, for example a mirror surface with the use of a reflective adhesive film.

Figure 21:
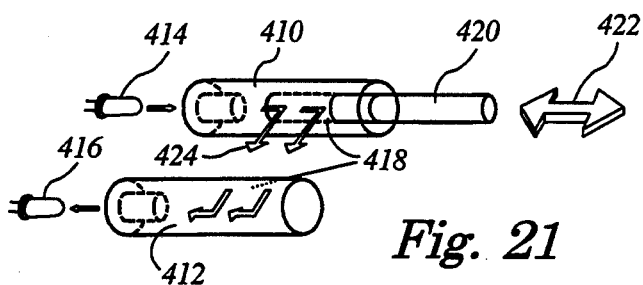

In the embodiment of the FIG. 21, a shadow rod 420 moves in a coaxial telescopical movement within a corresponding opening formed in the light pipe 410. The movement of the shadow rod is indicated by an arrow 422 in FIG. 21. Since the shadow rod 420 can extend through almost the entire length of the light pipe 410, it can intermittently block the light flow from the light source 414 or open the light flow from the light source 414, such that the light flow moves in the direction of arrows 424 to the light sensor 416 positioned within the light pipe 412.

Figure 22:
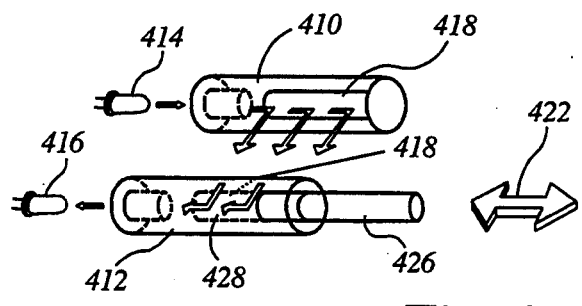

In an alternative embodiment of FIG. 22, the shadow rod 426 moves within an opening 428 made in the light pipe 412 to intermittently block the amount of light flow received by the sensor 416. In this embodiment the light pipe 410 does not have a shadow rod moving therein.

In FIG. 23, the embodiment illustrating dual input and single output circular tube sensor is shown. A shadow rod 430 which is mounted in coaxial sliding movement within the light pipe 410 not only controls the output of the light flow from the light emitting source 414, but also the input which reaches the light sensor 416 mounted within the light pipe 412. In addition, another shadow rod 432 mounted within an opening 434 in the light pipe 412 controls the input of light to the light sensor 416. Both shadow rods 430 and 432 move in the direction symbolically illustrated by their respective arrows 436 and 438. It should be noted; that the movement of each shadow rod 430 and 432 does not necessarily result in an equal output. For example, the output signal curves of each shadow rod do not have to be the same shape, when plotted.

Turning now to the embodiment shown in FIG. 24, a sensor suitable for extended displacements will be discussed. As can be seen in the drawing, the device is provided with an optical light pipe 440 having an opening 442 therein for receipt of a light source 444. The walls defining the opening 442 can be abraded in order to further diffuse the light being transmitted from the light source to the light sensor 446. A light receiving pipe 448 has a corresponding opening 450 therein which is defined by similarly abraded surface to still further diffuse the light received by the light source 446.

A translucent face 452 is formed on the surface of the light pipe 440 which faces the translucent face 454 of the light receiving pipe 448. The remaining sides of the lights pipes 440 and 448 can be covered with metallic stickers or other mirror reflective surfaces in order to channel the light in the desired direction of the facing surfaces 452 and 454. A shadow rod 456, in the embodiment shown in FIG. 24 formed in a triangular shape, moves between the light pipes 440 and 448 in the direction of arrow 458. If desired, a triangularly-shaped window can be made in the shadow rod 456 to permit a desired amount of light to pass from the light source 444 to the light sensor 446. Further, if desired, a spring means can be used for the shadow rod 456 to contact and provide some sort of a compliance feature. It is envisioned that this particular design can be particularly useful in displacements of three feet or more.

Referring now to the embodiment of FIG. 25, the use of a liquid as a light blocking means will be discussed. In the embodiment of FIG. 25 the optical sensor in accordance with the present invention is provided with a light emitter pipe 460 which houses a light emitting source 462. A translucent face 464 is formed on one of the surfaces of the light pipe 460 to allow a flow of light to exit the light pipe 460 in the direction of arrows 466.

A light receiver pipe 468 has a similar translucent face 470 formed on one of its faces to permit the light flow to enter the light pipe 468 and move in the direction of a light sensor 472 positioned within the light pipe 468. Both light pipes 460 and 468 are securely attached to a separation wall 474 at one of their ends. Securely attached to the wall 474 between the light pipes 460 and 468 is a liquid containing housing 476, which is shown in the drawing in the form of a cylindrical pipe. The wall 474 has a surface 478 to which the light pipes 460 and 468 are secured.

A rigid rectangular frame 480 is fixedly attached to the cylinder 476 at an end which extends through the wall 474 outwardly from the surface 478. The frame 480 extends between the light pipes 460 and 468 to be substantially in the path of the light flow emitted by the light source 462. Mounted within the frame 480 is a flexible collapsible, transparent liquid receiving tube 482 which is attached to the frame 480 by securing strips 484 extending along upper and lower lengths of the frame 480 to support and secure the tube 482.

The tube 482 is in a fluid communication with the interior of the liquid housing 476 and intermittently receives a colored liquid 486 therein. The liquid 486 can be a dark liquid to successfully block the light flow between the light pipes 460 and 468. A piston means 490 operates within the housing 476 to force the liquid 486 from the housing 476 into the tube 482 upon contact of a plate 492 with a tested surface. The piston 490 moves in the direction of arrow 494, coaxially within the housing 476 to force the liquid to flow into the collapsed tube 482 and block the light flow. In order to move the liquid back from the tube 482 into the housing 476, a pressurized air is formed within the device on the side of the wail, wherein the frame 480 is positioned. In this manner, once the pressure is no longer applied -.to the contact plate 492, the liquid 486 will be forced from the tube 482 into the housing 476.

Turning now to the embodiment of FIG. 26, the use of multiple light sensors and one light source will be discussed. As shown in FIG. 26, a singular light pipe 500 is surrounded by a plurality of light receiving pipes 502, with one of the light receiving pipes being removed to simplify explanation of the operation. Each of the receiving light pipes 502 houses at least one light sensor 504 to detect the light transmitted from the light pipe 500. Although not shown here, a light source connected in light transmitting relationship to the light pipe 500, for example a hollow cone of light, supplies the light to the pipe 500. In the embodiment shown in FIG. 26, the light pipe 500 is formed hollow, having an interior surface which is covered with non-reflective film to prevent "cross talk" between the sensors and also to channel the light in the desired direction.

The exterior surface 506 of the light pipe 500 is formed translucent to transmit the light from the entire circumference of the light emitting pipe 500. It is envisioned that a fiber optic bundle, cone-shaped, can also be used in place of a hollow cone of light for emitting the necessary light flow. The use of non-reflective surface on the interior of the light pipe 500 prevents any light sensor from detecting the movement of the shadow rod which belongs to another light pipe. This can alter the light flow and prevent the correct output signal of the light sensors 504.

Each sensor light pipe 502 is provided with its own shadow rod 508 which moves in the direction of arrows 510. The shadow rods 508 move in the space formed between the interior surface of the light sensor pipe 502 and the light emitting pipe 500. The inner surfaces of the light receiving pipes 502 are formed curved to correspond to the curvature of the inner cylindrical light emitting pipe 500. The inner surfaces 512 of the light receiving pipes 502 are formed translucent to allow the light flow to reach the light sensors 504. The remainder surfaces are made non-reflective, such as by covering with reflective adhesive film, schematically illustrated by dark surface 514.

The light pipes 502 are formed as separate segments of a tubular-shaped set of light sensors. Although not shown, spacers can be positioned within spaces 516 between the individual light receiving pipes 502, with the spacers preventing light flow between adjacent light receiving pipes 502.

Referring now to the embodiment of FIG. 27, the use of a multiple rotational shadow sensor is shown. A single light emitting pipe 520 has a light source 522 mounted therein. A pair of opposing light translucent surfaces (only one shown in FIG. 27 and designated by numeral 524) are formed on oppositely facing surfaces of the light pipe 520. On both sides of the light pipe 520 is a shadow disk 526 and 528, which have spiral windows 530 and 532, respectively, formed therein. Both disks are secured for simultaneous equidistant rotation on opposite sides of the light pipe 520 to a securing rod 534. The rod 534 rotates in the direction of arrows 536, thus transmitting torque to the disks 526 and 528 to intermittently align the windows 530 and 532 with the translucent surfaces 524 of the light emitting pipe 520.

A pair of light receiving pipes 538 and 540 are positioned on opposite sides of the shadow disks 526 and 528, respectively, so as to receive the light which passes through the windows 530 and 532 through their translucent surfaces and transmit the light flow to the light sensors 542 and 544. The remaining surfaces of the light pipe 520 and the light pipes 538 and 540 are covered with a non-transparent substance, such as metallic stickers, in order to properly channel the light in the desired direction. The spiral shadow disks can have different angular positions, if desired, and single output curve shapes. In a way, the shadow spiral disks 526 and 528, being connected to the same securing rod 534, will rotate at the same speed and in the same direction. If desired, additional sensors can be added to provide other outputs.

Turning now to the embodiments of FIGS. 28, 29 and 30 the use of a hollow cylindrical shadow rod is disclosed. In the embodiment of FIG. 28, the emitting light pipe 550 is enclosed within a hollow cylindrical tubular shadow housing 552. The emitter light pipe 550 is provided with a light source 554 positioned therein, and a translucent surface area 556 is formed on a surface portion of the pipe 550 facing a receiver light pipe 558. The light pipe 558, similarly to the light pipe 550, is enclosed and is surrounded by a hollow tubular shadow cylinder 560 which intermittently blocks and uncovers a translucent surface area 562 of the light receiving pipe 558.

A light sensor 564 is mounted within the light receiver pipe 558 to receive the light flow signal from the light emitter 554. The shadow cylinders 552 and 560 can move in a linear direction, symbolically illustrated by arrows 566 or in a circular direction illustrated by arrows 568. The shadow cylinders control the light flow by limiting the amount of light received by the light sensor 564 by moving either linearly or rotationally in any combination of linear and/or rotational input, and/or emitter, and/or receiver. As a result, the signal can have four inputs and one output.

The remainder surface areas of the light pipes 550 and 560 are covered with non-transparent substance, such as metallic stickers, to channel the light flow in the desired direction.

In the embodiment of FIG. 29, the shadow cylinder 570 is mounted in circumferentially enclosing relationship to a light emitter pipe 572, moving in either linear direction of arrow 574 or in the rotational direction of arrow 576. A light receiver pipe 578 has a translucent face 580 which faces a translucent face 582 of the light emitting pipe 572. The translucent faces 580 and 582 can be also formed on the shadow cylinder 570, as long as the translucent face is opposite the light receiving pipe 578.

In the embodiment of FIG. 30, the shadow cylinder 584 is mounted in circumferentially enclosing relationship about a light receiving pipe 586 and controls the amount of light which reaches the light sensor 588 through translucent faces 590. The light is emitted by a light source 592 mounted within a light emitting pipe 594. In this embodiment, similarly to the embodiment of FIG. 29, the shadow cylinder 584 can move either in a linear direction of arrow 596 or in the direction of rotational arrow 598. In both embodiments of FIGS. 29 and 30, the light flow is controlled from two possible different inputs, linear and rotational, with one output.

Turning now to the embodiment of FIG. 31, the optical displacement sensor, not shown in whole, is provided with an optical portion comprising a light emitting pipe 600 which houses a light source 602 within an opening 604 thereof, and a light receiving pipe 606, which houses a light sensor 608 in a correspondingly sized and shaped opening 610 thereof. The light emitting pipe 600 and light receiving pipe 606 are both provided with translucent areas 612 and 614, respectively, which allow the light to travel from the light source 602 in the direction of arrows 616 to the light sensor 608. A shadow rod, or plunger 618 is positioned between the light pipes 600 and 606 and travels in a linear direction illustrated by arrow 620.

A small window 622 is formed in the shadow rod, the window being smaller in size than the total surface area of either translucent surface 612 or 614. As a result, only a small amount of light flow will travel from the emitter 602 to the sensor 608.

As will be appreciated, the light transmitted from the light source 602 decreases as the light travels farther away from the light source. The change of position of the shadow rod 618 and its small window 622 varies the amount of light flow to the light sensor 608. Therefore, the position of the small window 622 determines the intensity, or amount of the light flow received by the light sensor.

By varying the size of the window 622, it is possible to program the output signal in a technical application. The light source 602 can be an infrared light emitting diode, and a light sensor 608 can be an infrared phototransistor.

Referring now to the embodiment of FIG. 32, the use of a "worm" shadow sensor will be discussed. A light emitter pipe 630 houses a light source 632 which is positioned in a correspondingly made openings 634. The light pipe 630 is provided with a translucent face 636 on one of the surface areas thereof to permit the light flow to exit the light pipe 630. A light receiving pipe 638 is positioned opposite the light pipe 630 and houses a light sensor 640 therein. A similar translucent face 642 is made in the receiving light pipe 638 to allow input of the light flow into the light pipe 638 and detection of the light flow by the light sensor 640. A shadow rod 643 is positioned between the light pipes 630 and 638, such that the movement of the shadow rod in the linear direction of arrow 644 and/or rotational direction shown by arrow 646 intermittently blocks or uncovers the light path for the light flow.

A window 648 is made in the shadow rod 643 for intermittently blocking or uncovering the light path. The shadow rod 643 has an upper edge 650, a portion of which is formed with a worm rack 652 in a form of a plurality of equidistantly spaced serrations, or teeth. Adapted for engaging the rack 652 is a rotating worm 654 which accepts application of a torque transmitted by an external source (not shown) to force linear movement of the shadow rod 643.

It should be noted that no light is allowed to pass through and/or over the rack 652. As a result, a multi-rotational shadow sensor is created, which allows more than 360° of rotation to be received before the maximum and minimum extremes of the light flow are reached. Different inputs can be received through the use of a certain number of rotations applied to the worm 654 to drive the shadow rod 643. It is envisioned that this particular design can replace the multi-rotational potentiometers, for example the potentiometers of 3-turn, 5-turn, 10-turn, etc. capabilities.

Turning now to the embodiment of FIG. 33, the optical displacement sensor discloses the use of a single light emitter pipe 660 provided with a light source 662 mounted therein. A translucent surface 664 is formed in one of the faces of the light pipe 660 to direct the light from the light emitter pipe 660 to a stack of light receiving pipes (in this embodiment the receiving pipes 666 and 668) and to dual light sensors 670 and 672. The receiving light pipes 666 and 668 are provided with translucent surfaces 674 and 676, respectively, to allow passing of the light flow through the light pipes to the light sensors. A shadow rod 678 is mounted between the opposing faces of the light pipe 660, receiver light pipes 666 and 668.

An opening window 680 is formed in the shadow rod 678, so that a light flow can pass through the window, when in alignment with the surfaces 664, 674 and 676. At other times, the light flow will be blocked by the shadow rod 678. As can be seen in the drawing, not all light emitted by the light source 662 will reach the sensors 670 and 672, since some of the light flow, the portion schematically shown by arrows 682, will be blocked by the body of the shadow rod 678. The shadow rod 678 moves in the direction of arrows 684 to intermittently block the light flow to the window 680. Although not shown, an opaque and/or reflective film is positioned between the contacting surfaces of the light pipes 666 and 668 along the plane 686. This nontransparent layer will prevent any light flow between the receiver light pipes 666 and 668 and thereby minimize the "cross-talk".

It is envisioned that the outputs of the light receiver pipes 666 and 668 can change. If output of the receiver pipe 666 is not equal to output of the receiver pipe 668, then there is a change in the direction of movement of the shadow rod 678, as shown by arrows 690, indicating shear in that direction. If the output of light pipe 666 is equal to the output of the light pipe 668, it will signify that there is no shear in the direction of movement of plunger shown by arrows 690. The dual light sensors, as shown in FIG. 33, can be successfully used to detect displacement within a plane in which a plunger (not shown but attached to the end 692 of the shadow rod 678) moves.

Referring now to the illustration of FIGS. 34, 35 and 36, various designs of the shadow rod and/or a window within the shadow rod are disclosed. FIG. 34 illustrates a combination of two individual shadow rods for light sensors. The triangle 700 is particularly useful for analog signals, while the strip 702, provided with a plurality of windows 704 in the body thereof, is particularly useful for digital applications. The single output generally decreases as more light is blocked, yet the digital strip 702 forces the signal to increase and decrease within a certain band. The output signal looks like a wavy line drawn along two opposite diagonal points of a rectangle.

The digital strip 706 of the embodiment shown in FIG. 35 is similarly provided with a plurality of equidistantly spaced identical windows 708, which produces a "flatter" signal in comparison with the output signal received through the use of the embodiment shown in FIG. 34. The output signal will still be a wavy line drawn between the two opposite diagonal points of a rectangle, except that the rectangle itself will be flatter. The displacement axis "X" is the horizontal axis, while the signal output, typically volts or amperes is quoted on the vertical axis.

In the embodiment of the FIG. 36, an optional shape for the shadow rod and/or its window is shown. This particular design provides a single output, a cross between analog signal of the analog triangle 700 and the digital strip 702. The design of FIG. 36 provides for a signal that has a varying output, yet has some signals that are constant on the output.

Referring now to FIGS. 37 and 38, still further embodiments of the optical portion of the design in accordance with the present invention will be discussed. Shown in FIG. 37 is an emitter light pipe 710 with its associated light source 712. A similarly elongated light receiver pipe 714 is mounted opposite the emitter light pipe 710 and has a light sensor 716 mounted therein. A translucent face 718 is formed adjacent an opposite end 720 of the light emitter pipe 710, and an opposing translucent face 722 is made at the distant end of the light receiver pipe 714.

The light travels from the light source 712 in the direction of arrows 724 to the translucent face 718 and reaches the light sensor 716 through the translucent face 722. A shadow rod 726 moves between the translucent faces 718 and 722 in the direction of arrows 728 blocking and uncovering the light flow travelling from the face 718 to the face 722. It is possible to transmit the light through the entire extended length of the light pipes 710 and 714 through the use of fiber optic cables. It is envisioned that the extended light pipes reduce the electromagnetic interference (EMF) which usually affects copper wires running between long distances. By locating the translucent surfaces at the distant ends of the light pipes 710 and 714, a further reduction of the EMF can be achieved.

In the embodiment shown in FIG. 38, a shorter light emitter pipe 730 having a translucent face 732 transmits a flow of light from the light source 734 to a translucent face 736 of an elongated (extended) light receiver pipe 738 having fiber optic cables mounted therein, and to a light sensor 740. The light sensor 740 is mounted at the opposite end of the light pipe 738 than the translucent light receiving face 736. A shadow rod 742 moves in the direction of arrows 744 between the translucent faces 732 and 736 blocking and uncovering the light flow. This design will also be useful in reducing the EMF which usually affects copper wires running between long distances. It is possible to connect the light source 712 and 734, as well as the light sensors 716 and 740 exteriorly to the light pipes 710, 714, 730 and 738, respectively.

However, in the embodiment of FIG. 39, the light emitter pipe 750 can be made as a unitary body with a light source 752, while the light receiving pipe 754 can be made as one piece with a light sensor 756. The translucent surfaces 758 are formed at the ends of the light pipes 750 and 754 opposite the area of positioning of the light source 752 and the light sensor 756. A shadow rod 760 moves between the light pipes 750 and 754 blocking the light flow from the light source 752 to the light sensor 756. The direction of the shadow rod is schematically illustrated by arrows 762. The translucent faces 758 are built into the one piece light sensor and light source/pipe units.

Turning now to the embodiment of FIG. 40, the use of one piece translucent light sensor and a one piece translucent light source mounted within elongated housings is disclosed. The emitter light pipe housing 764 is provided with a "built in" light source 766 and an elongated translucent face 768, which is mounted opposite a similarly extended translucent face 770 of a receiver light pipe 772, which has a built-in light sensor 774. A shadow rod 776 moves in the direction of arrow 778 between the translucent faces 768 and 770 to control the light flow which reaches the light sensor 774. These elongated light pipes or lens housings are substituted for the light pipes of previously described embodiments.

As shown in FIG. 41, it is possible to change the light flow path from a generally "C"-shape to an "S"-shape or a "Z"-shape. The embodiments discussed in many of the above cases created a C-shaped light flow path, wherein the light flow is emitted in a certain direction, then channeled at approximately 90 degrees to the original direction and is channeled again into a path substantially perpendicular to the second stage and parallel, but reverse, to the first stage.

As can be seen in FIG. 41, by positioning the light source 780 in a chamber 782 formed in the end 784 of the light pipe 786, and by positioning the light sensor 788 in the chamber 790 of the receiving light pipe 792, the path of the light flow can be amended to become a S-shape by causing the light flow to follow the path designated generally by arrows 794. The arrows show that the light flow is emitted by the light source 780 and travels in a linear direction before it is channeled in a substantially perpendicular direction designated by arrows 796 through a translucent face 798 of the light pipe 786.

The light flow then passes through a window 800 formed in the shadow rod 802 and is further channeled to the translucent face 804 of the light pipe 792. The light flow then changes its direction, as shown by arrows 806, at approximately a right angle to the direction of the light path shown by arrows 794 and is then transmitted to the sensor 788, which measures the amount of light flow. During the operation of the device, the shadow rod 802 moves in the direction of arrow 808 in a linear orientation.

By utilizing the amended light flow path it is possible to obtain a more linear output signal, when measuring a change in the displacement of the sensor. It will also provide a manufacturing option for the optical transducer in accordance with the present invention. As will be appreciated, by mounting the light source 780 and the light sensor 788 in the opposite ends of the light pipe 786 and 792, respectively, the light flow path can be changed to have a Z-shape. As was mentioned above, the present design allows to achieve a more linear output signal curve, since the light source is placed opposite a less sensitive end of the receiving light pipe, while the light sensor is placed opposite the less brighter end of the emitter light pipe.

Turning now to the embodiment of FIG. 42, a method of forming an altered signal curve output is illustrated. As can be seen in the drawing, the light emitting pipe 820 is provided with a translucent light emitting face 822 on one of the surfaces thereof. The face 822 is defined by a straight edge 824 at least in a portion of its perimeter.

A light source 826 is positioned in an opening 828 made in the light pipe 820 to provide a light flow in the direction of arrows 830, towards a light receiving means 832.

The light receiving pipe 832 is provided with a light receiving face 834 on that surface thereof which faces the light emitting pipe 820. The light receiving face 834 is defined by a perimeter, at least a portion of which is defined by a curved edge 836.

The light receiving pipe 832 is provided with a light sensor 838 mounted therein for detecting the amount of light transmitted from the face 822 to the face 834. As a result, the sensor has a different signal output curve from the signal which the light source 826 emits. A plunger 840 intermittently blocks the light flow 830 by alternatively aligning a window 842 with the faces 822 and 834 or by blocking all or portions thereof. As shown in FIG. 42, the plunger moves in a linear direction schematically illustrated by arrow 848. An optional second light sensor 844 calibrates and monitors light source output. If desired, the second light sensor can be omitted.

Referring now to the embodiment of FIG. 43, a light pipe 850 is shown to house a light emitting diode 852 mounted in an opening 854 thereof. A light emitting translucent face 856 is formed on one of the surfaces of the light pipe 850 to emit the light in the direction of arrows 858 towards a light receiving pipe 860 which houses a light sensor 862.

In this embodiment, a translucent face 864 is formed on that surface of the light pipe 860 which is opposite a surface 866 facing the light emitting pipe 850. A cover 870 which is sized and shaped to substantially correspond to the shape of the face 864 is fixedly attached to the translucent face 864. The cover 870 can be made from a reflective material, such as a reflective adhesive film.

Since the translucent face 864 is on the farthest side away from the flow path 858, the light is redirected to the light sensor 862 in a later stage of the light flow. The reflective cover 870 tends to redirect the light from translucent face 864 back into the light sensor light pipe 860. It is envisioned that by using this method a more effective way of channeling the light towards the light sensor can be achieved.

Mounted between the light pipes 850 and 860 is a light blocking means in the form of a plunger 872 having a window 874 formed therein. The plunger 872 moves in a linear direction shown by arrow 876 intermittently blocking the light flow 858 and interrupting the light flow at preselected intervals.

Referring now to the embodiment of FIG. 44, a method of redirecting the light within the light receiving means and to the light sensor at a later stage is achieved through a provision of a reflective adhesive cover 880 attached to a light emitting pipe 882 to that portion of the surface thereof which has a translucent face 884. The face 884 is opposite the face 886, through which the light flow indicated by arrow 888, leaves the light pipe 882. The light flow is produced by a light emitting diode 890 which is housed within the light pipe 882.

A light receiving pipe 892 is likewise provided with a translucent face 894 which is opposite a face 896, through which the light is admitted into the light pipe 892. In this manner, the light sensor 898 will receive the signal at a later stage.

A linearly moving plunger 900 moves in the direction of arrow 902 intermittently blocking the light flow 888, or blocking at least a portion thereof.

In the embodiments of FIGS. 42, 43 and 44 all other surfaces of the light pipes are covered with metallic stickers in order to channel the light in the desired direction.

The embodiments described herein disclose the use of a solid body or liquid as a light blocking means. It is envisioned that gas can also be used for these purposes. Additionally, a change in the light spectrum, for example from red to blue, can also be a light blocking means. The light blocking means can be also used in combination with a spring or the liquid tubes within a pressurized chamber. Further, the light pipes can be moved in relationship to each other instead of using a shadow rod to interrupt a light flow.

The displacement sensor in accordance with the present invention can be successfully used to replace potentiometers in the joystick to provide high reliability, increased resolution and simple manufacturing. The single output can be shaped to desired output preference, and the sensor will be resistant to EMI.

The displacement sensor of the present invention can be also used to replace potentiometer or contact leaf switch in commercial video game joysticks with the same advantages. Further, the displacement sensor can be used as a replacement for strain gauge type pressure sensors to provide greater resistance to pressure spikes, ease of manufacturing, resistance to EMI and lower power consumption. It can be also used as a replacement for rotary potentiometers and linear potentiometers of wire wound, carbon and plastic types for such consumer and industrial uses as T.V.s, volume controls, etc. to provide for higher reliability, resolution and ease of manufacturing.

As with the previous replacement applications, the temperature range can be compensated for. The displacement sensor of the present invention can be also used as a replacement for displacement and dimensional linear variable differential transducers. It will afford a higher sensitivity than traditional LVDTs, ease of manufacturing, higher resistance to EMI. The sensors of the present invention have lower power consumption, they are unaffected by large metal objects, making installation easier, and the temperature range can be compensated for like in all other LVDTs. The displacement sensor can also be used as a replacement for rotary and linear optical encoders to provide for higher resolution, ease of manufacturing, lower power consumption, resistance to EMI. Additionally, the optical displacement sensor can be used as a replacement for traditional solid state sensors, optielectronic sensors and devices, positional sensors (digital and analog), current sensors, temperature sensors, airflow sensors, etc.

As a product enhancement element it can be used in motion/shock detection systems to replace a liquid mercury switch which measures the movement of the magnetic field, for example in car alarms. It can be successfully used in robot tactile applications to form a tactile transducer, as an end effector (of the hand and fingers), or can be used in force feedback in robots. The advantages would include higher reliability than traditional carbon potentiometers or plastic potentiometers, high resolution, ease of manufacturing, resistance to EMI, lower power consumption. The signal output can be shaped to a desired preference and temperature range can be compensated for, when the sensor of the present invention is used.

Additionally, it is envisioned that the optical sensor can be used in the field of prosthesis manufacturing to assist the prosthetic users in determining the amount of force applied in handling objects, such as a glass of water or an empty paper cup. It can be used in artificial limbs to force an electrical tactile feedback to the patient. The sensor would provide higher reliability than traditional carbon potentiometers or plastic potentiometers, high resolution, ease of manufacturing, resistance to EMI, lower power consumption. Signal output can be shaped to the desired preference and temperature range can be compensated for. It is envisioned that the sensor can also be used in gyroscopes, accelerometers, and velocity meters. Similarly, it can be used as a velocity and pressure sensor feedback in musical instruments, in handheld pocket video games, home video games, as a position feedback of auto focus cameras and video cameras to determine position of the lens and other uses. It can also be used to control the positioning of helicopter blades, specifically the angle of the blades used in determining the amount of lift, to determine shock absorber position in cars, trucks, and other vehicles when used in active suspension systems in multi-terrain vehicles to determine the angular position of the rear wheels, to determine position of a lens in photocopier enlargement devices, to provide better control than traditional step-up motors for disk drives, to detect deceleration of a car to trigger airbag release mechanisms, to enhance virtual reality with actual sensing of arm and leg movements to feedback the position of arm and leg to simulators. In general, the displacement sensor can be used in any number of applications, wherein detection of position or movement is necessary.

Many changes and modifications can be made within the design of the present invention without departing from the spirit thereof. We, therefore, pray that our rights of the present invention be limited only by the scope of the appended claims.

We claim:

1. An optical displacement transducer, comprising:
   an elongated hollow housing having a central chamber therein;
   a partition dividing the central chamber into a first portion and a second portion, said partition having a central opening therein;
   a light emitting means mounted in the first portion of the central chamber;
   a light receiving means mounted opposite said light emitting means in the first portion of the central chamber; and
   an axially movable light blocking means extending between the light emitting means and the light receiving means for intermittently, at least partially, blocking the light emitted by said light emitting means.

2. The device of claim 1, wherein said light blocking means moves between a fully extended position, allowing substantially all light emitted by the light emitting means to travel to the light receiving means, and a second position at least partially blocking the light.

3. The device of claim 1, further comprising a compressible means positioned within the second portion of the central chamber.

4. The device of claim 3, wherein said light blocking means has an inner end, and said compressible means contacts said inner end, continuously urging the light blocking means into a fully extended position.

5. The device of claim 1, wherein said light blocking means comprises an elongated rod having a light transmitting window made adjacent to one of its ends.

6. The device of claim 5, wherein said central opening is sized and shaped to receive the rod in a sliding engagement therethrough.

7. The device of claim 5, wherein said housing has a closed end blocked by an end plate having an opening, through which the rod protrudes outwardly from the housing.

8. The device of claim 5, wherein said elongated rod has an inner end which carries an end plate thereon, said end plate frictionally contacting inner walls of the housing.

9. The device of claim 8, wherein said end plate contacts the partition, said partition limiting movement of the rod outwardly.

10. The device of claim 1, wherein said light emitting means comprises a light emitting diode.

11. The device of claim 10, wherein said diode is an infrared light emitting diode.

12. The device of claim 10, wherein said light emitting means further comprises an emitter light pipe housing the light emitting diode therein.

13. The device of claim 12, wherein said emitter light pipe has a surface which faces the light blocking means, said surface having a translucent portion allowing light to travel out of the emitter light pipe.

14. The device of claim 1, wherein said light receiving means comprises a phototransistor.

15. The device of claim 14, wherein said phototransistor is an infrared phototransistor.

16. The device of claim 14, wherein said light receiving means further comprises a receiving light pipe which houses the phototransistor therein.

17. The device of claim 16, wherein said receiving light pipe has a surface which faces the light blocking means, said surface having a translucent portion allowing light to travel to the phototransistor through the receiving light pipe.

18. An optical displacement transducer, comprising:
   an elongated hollow housing having a central chamber therein;
   a partition dividing the central chamber into a first portion and a second portion, said partition having a central opening therein;
   a light emitting means mounted in the first portion of the central chamber, said light emitting means comprising a light emitting diode mounted within an emitter light pipe;
   a light receiving means mounted opposite said light emitting means in the first portion of the central chamber, said light receiving means comprising a phototransistor and a receiving light pipe;
   an axially movable light blocking means extending between the emitter light pipe and the receiving light pipe, said light blocking means comprising an elongated rod having a light transmitting window made adjacent to one of its ends, an inner end of the rod carrying an end plate which contacts the partition to limit travel of the rod outwardly from the housing, said elongated rod moving between a first position, when said light transmitting window is in alignment with the emitter light pipe and the receiving light pipe, and a second position when said light transmitting window is in at least partial misalignment with the emitter light pipe and the receiving light pipe.

19. The device of claim 18, wherein said emitter light pipe has a surface which faces the elongated rod, at least a portion of said surface being translucent to allow light to travel out of the emitter light pipe.

20. The device of claim 19, wherein said receiving light pipe has a surface which faces the elongated rod, at least a portion of said surface being translucent to allow light to travel into the receiving light pipe.

21. The device of claim 18, wherein said light emitting diode is an infrared light emitting diode.

22. The device of claim 18, wherein said phototransistor is an infrared phototransistor.

23. The device of claim 18, wherein said central opening in the partition is sized and shaped to receive the rod in a sliding engagement therethrough.

24. The device of claim 18, wherein said housing has a closed end blocked by an end plate having an opening, through which the rod protrudes outwardly from the housing.

25. An optical displacement transducer, comprising:
 an elongated hollow housing having a central chamber therein;
 a partition dividing the central chamber into a first portion and a second portion, said partition having a central opening therein;
 a compressible means positioned within the second portion of the central chamber;
 a light emitting means mounted in the first portion of the central chamber;
 a light receiving means mounted opposite said light emitting means in the first portion of the central chamber; and
 an axially movable light blocking means extending between the light emitting means and the light receiving means for intermittently, at least partially, blocking the light emitted by said light emitting means.

26. The device of claim 25, wherein said light blocking means has an inner end, and said compressible means contacts said inner end, continuously urging the light blocking means into a fully extended position.

27. The device of claim 25, wherein said light blocking means is adapted for movement between a fully extended position, allowing substantially all light emitted by the light emitting means to travel to the light receiving means, and a second, compressed position, at least partially blocking the light.

28. The device of claim 25, wherein said light blocking means comprises an elongated rod having a light transmitting window adjacent to one of its ends.

29. The device of claim 28, wherein said elongated rod has an inner end which carries an inner end plate thereon, said inner end plate frictionally contacting the inner walls of the housing.

30. The device of claim 29, wherein said inner end plate has a surface, which contacts the partition, said partition limiting movement of the rod outwardly.

31. The device of claim 28, wherein said housing has a closed end blocked by an outer end plate which has an opening, through which the rod protrudes outwardly from the housing.

32. The device of claim 25, wherein said diode is an infrared light emitting diode.

33. The device of claim 32, wherein said light emitting means further comprises an emitter light pipe housing the light emitting diode therein.

34. The device of claim 33, wherein said emitter light pipe has a surface which faces the light blocking means, said surface having a translucent portion which allows light to travel out of the emitter light pipe.

35. The device of claim 34, wherein said light receiving means comprises a phototransistor.

36. The device of claim 35, wherein said phototransistor is an infrared phototransistor.

37. The device of claim 35, wherein said light receiving means further comprises a receiving light pipe which houses the phototransistor therein.

38. The device of claim 37, wherein said receiving light pipe has a surface which faces the light blocking means, said surface having a translucent portion which allows light to travel to the phototransistor through the receiving light pipe.

39. An optical displacement transducer device comprising:
 a light emitting means for emitting a light flow;
 a light receiving means for receiving the light flow mounted opposite said light emitting means; and
 a means for intermittently blocking at least in part, the light flow from said light emitting means; and
 a means associated with at least said light emitting means for distributing the light flow by diffusion.

40. An optical displacement transducer device, comprising:
 a light emitting means for emitting a light flow;
 a light receiving means for receiving the light flow mounted opposite said light emitting means, wherein said light emitting means comprises a housing having a light source positioned therein, said housing having a light permeable face in at least that portion thereof which faces the light receiving means; and
 a means for intermittently blocking, at least in part, the light flow from said light emitting means.

41. The device of claim 40, wherein said housing has a rectangular solid shape, and an opening is formed in one end thereof for receiving said light source therein.

42. The device of claim 40, wherein said light permeable face has a perimeter, at least a portion of which is defined by a straight edge.

43. The device of claim 40, wherein said light receiving means comprises at least one body having a light sensor mounted therein, and a light permeable face formed in that portion of the body which faces the light permeable face of the light emitting housing.

44. The device of claim 43, wherein said light sensor is positioned in an end of the light receiving housing distant from the light permeable face.

45. An optical displacement transducer comprising:
 a light emitting means for emitting a light flow;
 a light receiving means for receiving the light flow mounted opposite said light emitting means, wherein said light emitting means comprises a housing and a light source connected to the housing in light transferring relationship, said housing being light permeable in at least a portion thereof for transmitting the light flow from said light source to an exterior of the housing; and
 a means for intermittently blocking, at least in part, the light flow from said light emitting means.

46. The device of claim 45, wherein said light source is positioned in an end of the housing distant from said light permeable face.

47. The device of claim 45, wherein said light receiving means comprises at least one light receiving body having a light sensor mounted therein and a light permeable face formed in that portion of the body which faces the light permeable face of the light emitting means, the light flow travelling from the light source to the light sensor along a path having a generally C-shaped configuration.

48. An optical displacement transducer device, comprising:
a light emitting means for emitting a light flow;
a light receiving means for receiving the light flow mounted opposite said light emitting means, wherein said light receiving means comprises at least one body having a light permeable face formed in at least that portion of said at least one body which faces the light emitting means; and
a means for intermittently blocking, at least in part, the light flow from said light emitting means.

49. The device of claim 48, wherein said at least one body has a generally rectangular solid shape, one end of said at least one body being provided with an opening for retaining the light sensor therein.

50. The device of claim 48, wherein said light permeable face of said at least one body has a perimeter, at least a portion of which is defined by a straight edge.

51. An optical displacement transducer device comprising:
a light emitting means for emitting a light flow;
a light receiving means for receiving the light flow mounted opposite said light emitting means; and
a means for intermittently blocking, at least in part, the light flow from said light emitting means, wherein said light blocking means comprises at least one solid light impermeable member moving between a first position, at least partially blocking the light flow from the light emitting means and a second position, allowing substantially entire light flow to pass to the light receiving means.

52. The device of claim 51, wherein said at least one solid member moves between said light emitting means and said light receiving means.

53. The device of claim 51, wherein said at least one solid member is provided with a window which is moved in general co-alignment with the light flow when the solid member is in the first position to permit the light flow to pass therethrough.

54. The device of claim 53, wherein said at least one solid member is adapted for a linear movement in a plan generally parallel to normal axes of the light emitting means and the light receiving means.

55. The device of claim 53, wherein said window is generally sized and shaped to permit substantially entire light flow to pass therethrough.

56. The device of claim 53, wherein said window is generally sized and shaped to permit only a limited light flow to pass therethrough.

57. The device of claim 53, wherein said window has a longitudinal axis which is substantially parallel to a longitudinal axis of the solid member, and of said light emitting means and said light receiving means.

58. An optical displacement transducer, comprising:
a light emitting means comprising a housing having an interior chamber formed therein for housing a light source and a translucent face for channeling a light flow emitted by the light source to an exterior of the housing;
a light receiving means mounted opposite the housing and comprising a light receiving body having an interior chamber formed therein for receiving a light sensor therein to detect the amount of light received by the body, said body having a translucent face for channeling the light to the light sensor; and
a light blocking means mounted between the housing and the light receiving body and movable in a linear direction for intermittently blocking the light flow from the light source to the light sensor, said light blocking means comprising a solid member having a window therein to allow the light flow to pass therethrough.

59. The device of claim 58, wherein the light flow is channeled along a path having a general "C"-shape.

* * * * *